US006840908B2

(12) United States Patent
Edwards et al.

(10) Patent No.: US 6,840,908 B2
(45) Date of Patent: Jan. 11, 2005

(54) SYSTEM AND METHOD FOR REMOTELY ADMINISTERED, INTERACTIVE HEARING TESTS

(75) Inventors: Brent W. Edwards, San Francisco, CA (US); Christoph Menzel, Madison, CT (US); Sunil Puria, Mountain View, CA (US)

(73) Assignee: Sound ID, Palo Alto, CA (US)

( * ) Notice: Subject to any disclaimer, the term of this patent is extended or adjusted under 35 U.S.C. 154(b) by 0 days.

(21) Appl. No.: 09/977,019

(22) Filed: Oct. 12, 2001

(65) Prior Publication Data

US 2003/0083591 A1 May 1, 2003

(51) Int. Cl.$^7$ .............................. A61B 5/00; A61B 5/12
(52) U.S. Cl. ...................................... 600/559; 73/585
(58) Field of Search ............................... 600/300, 559; 73/585; 381/124

(56) References Cited

U.S. PATENT DOCUMENTS

| | | | |
|---|---|---|---|
| 3,808,354 A | | 4/1974 | Feezor et al. |
| 4,284,847 A | | 8/1981 | Besserman |
| 5,197,332 A | | 3/1993 | Shennib |
| 5,737,389 A | | 4/1998 | Allen |
| 5,811,681 A | | 9/1998 | Braun et al. |
| 5,868,683 A | | 2/1999 | Protopapas et al. |
| 5,928,160 A | | 7/1999 | Clark et al. |
| 6,022,315 A | | 2/2000 | Iliff |
| 6,061,431 A | | 5/2000 | Knappe et al. |
| 6,319,207 B1 | * | 11/2001 | Naidoo ........................ 600/559 |
| 6,322,521 B1 | | 11/2001 | Hou ............................ 600/559 |
| 6,379,314 B1 | * | 4/2002 | Horn ........................... 600/559 |
| 6,428,485 B1 | * | 8/2002 | Rho ............................ 600/559 |
| 6,522,988 B1 | | 2/2003 | Hou |
| 2002/0076056 A1 | * | 6/2002 | Pavlakos ...................... 381/60 |

FOREIGN PATENT DOCUMENTS

| | | | |
|---|---|---|---|
| DE | 19600234 | 7/1997 | |
| DE | 29905172 | 6/1999 | |
| DE | 19815373 | 10/1999 | |
| WO | WO 00/64350 | 11/2000 | |
| WO | WO 01/26272 | 4/2001 | |
| WO | WO 200126272 A2 | * 4/2001 | ........... A61B/05/12 |
| WO | WO 01/52737 | 7/2001 | |

OTHER PUBLICATIONS

U.S. Provisional Application No. 60/177,695, Filed Jan 24, 2000 entitled *Remote Hearing Test*, inventor Zezhang Hou.

(List continued on next page.)

*Primary Examiner*—Charles Marmor
(74) *Attorney, Agent, or Firm*—Mark A. Haynes; Haynes Beffel & Wolfeld LLP

(57) ABSTRACT

A technique allows a web site visitor, or other user of a consumer electronics device that is remote from a hearing test server, to measure their hearing loss in an efficient and consistent way which is self-administered, and to store the measurements as a hearing profile which can be used for customizing audio products. The technique includes a method for conducting a hearing test using a computer program. The method includes establishing a communication channel between a remote device and server in a communication network. A first component of the computer program is executed on the server, and a second component of the computer program is executed at the remote device. The computer program according to the invention comprises a routine to manage interaction via an interface on the remote device, and adaptively select stimuli based upon the interaction to be produced at the remote device according to a convergent process to determine a hearing characteristic. The interaction comprises an N-alternative forced choice interaction in one embodiment. The convergent process comprises a staircase function or a maximum likelihood function in alternative embodiments of the invention.

48 Claims, 23 Drawing Sheets

OTHER PUBLICATIONS

U.S. Provisional Application No. 60/189,010, Filed Mar. 13, 2000 entitled *Method and System for On–Line Hearing Examination and Correction*, inventor Zezhang Hou.

U.S. Patent Application No. 09/728,623, Filed Dec. 1, 2000 entitled *Adaptation of Audio Data Files Based On Personal Hearing Profiles*, inventor Ali Mouline.

Braida, L.D. et al., "Review of Recent Research on Multi-band Amplitude Compression for the Hearing Impaired," Studebaker, G.A., et al. eds., The Vanderbilt Hearing–Aid Report, Upper Darby, Pennsylvania: Monographs in Contemporary Audiology (1982), 133–140.

Lippman, R.P., et al., "Study of Multichannel Amplitude Compression and Linear Amplification for Persons with Sensorineural Hearing Loss, " J. Acoust. Soc. Am. (Feb. 1981) 524–534.

Villchur, E., "Signal Processing to Improve Speech Intelligibility in Perceptive Deafness," J. Acoust. Soc. Am. 53(6) (1973), 1646–1657.

http://www.audiologyawareness.com/ Web site providing survey–type hearing assessment tests, date of publication unknown. URL reg. as early as Nov. 24, 1997.

* cited by examiner

SYSTEM AND METHOD FOR REMOTELY ADMINISTERED, INTERACTIVE HEARING TESTS

RELATED APPLICATION DATA

The present application is related to co-pending and commonly owned U.S. patent application Ser. No. 09/830,480, INTERNET BASED HEARING ASSESSMENT METHODS, invented by Menzel et al.; filed 26 Apr. 2001; and to co-pending and commonly owned U.S. patent application Ser. No. 09/975,863, SYSTEM AND METHOD FOR REMOTELY CALIBRATING A SYSTEM FOR ADMINISTERING INTERACTIVE HEARING TESTS, invented by Menzel, et. al; filed on the same day as the present application.

BACKGROUND OF THE INVENTION

1. Field of the Invention

The present invention relates to methods and systems for remotely administering hearing tests, in which the subjects of the test use consumer electronic equipment coupled to communication media, such as Internet connected personal computers, cell phones, personal digital assistants, personal audio equipment, and the like, for the generation of stimuli during the test.

2. Description of Related Art

Hearing tests are used to develop hearing profiles of persons, which can be used for fitting hearing aids and for other diagnostic purposes. Professional audiologists are typically required for conducting the tests needed to provide a hearing profile, because of the large number of factors involved in making an assessment necessary for generating a reliable hearing profile. An audiologist is able to set up a controlled environment, and conduct the test according to a testing protocol involving a number of stimuli and response steps that is adapted based on the responses gathered during the test.

The hearing profiles of individuals vary in a number of ways. The ability to hear sounds varies with frequency among individuals across the normal audio frequency range. Also, the dynamic range varies among individuals so that levels of an audio stimulus that are perceived as soft sounds and levels of an audio stimulus that are perceived as loud sounds differ from person to person. Standard hearing tests are designed to produce an audiogram that characterizes such factors as frequency, sensitivity and dynamic range in the hearing profiles of individuals. There are also other factors that affect a hearing profile. For example, psychoacoustic factors concerning the manner in which a person perceives combinations of normal sounds affect the ability to hear in ways that can vary from person to person. Also, environmental factors such as the usual listening environment of a person (library, conference room, concert hall) and the equipment on which the sound is produced (loud speakers, ear phones, telephone hand set) are important. In persons wearing hearing aids or using other assistive hearing devices, the type of aid or device affects the hearing profile. The physiology of an impairment suffered by the individual may also be an important factor in the hearing profile.

The hearing profiles of individuals have been applied in the hearing aid field for customizing and fitting hearing aids for individuals. See, for example, U.S. Pat. No. 4,731,850 entitled PROGRAMMABLE DIGITAL HEARING AID SYSTEM, invented by Levitt et al.; and U.S. Pat. No. 5,848,171 entitled HEARING AID DEVICE INCORPORATING SIGNAL PROCESSING TECHNIQUES, invented by Stockham, Jr. et al. Thus, techniques for processing sound to offset variations in hearing are well known. However, these techniques are unavailable to persons not using hearing aids. Furthermore, many persons who could benefit from such processing are not in position to use hearing aids for a variety of reasons.

A variety of uses for hearing profiles, other than for the purposes of prescribing hearing aids and assistive listening devices, is being developed. For example, hearing profiles of individuals can be utilized for producing customized audio products, such as pre-recorded music that has been modified according to the hearing profile of the listener. One medium for delivering customized audio products is the Internet. See, co-pending U.S. patent application Ser. No. 09/957,344, entitled SOUND ENHANCEMENT FOR MOBILE PHONES AND OTHER PRODUCTS PRODUCING PERSONALIZED AUDIO FOR USERS, invented by Rader, et al. filed 20 Sep. 2001; and co-pending U.S. patent application Ser. No. 09/464,036, entitled SYSTEM AND METHOD FOR PRODUCING AND STORING HEARING PROFILES AND CUSTOMIZED AUDIO DATA BASED ON SUCH HEARING PROFILES, invented by Pluvinage, et al., filed 15 Dec. 1999.

Because of the difficulty in obtaining a hearing assessment test, and for a variety of other reasons, many persons who could benefit from devices that would assist their hearing do not follow through with obtaining a prescription for such devices. Thus, it is desirable to simplify the procedures involved in obtaining a reliable hearing assessment.

U.S. Pat. No. 5,928,160 describes a home hearing test system and method based on the use of calibrated headphones specially manufactured to support the hearing test using home audio equipment. In addition, reference is made to this patent for its discussion of background concerning hearing assessment tests in general. However, home hearing assessment tests have not achieved commercial acceptance.

Some efforts have been made to develop a technique for allowing a web site visitor to measure their hearing loss in an efficient and consistent way that is self-administered. Some of these attempts have implemented procedures that are similar to if not identical to a clinical audiogram, where a tone is presented and the listener responds if they heard the sound, in a type of yes-no threshold test. Other attempts implement a screening procedure where tones are presented and results are based on whether or not you heard those tones with no adjustment of sound presentation based on user response.

The yes-no procedures of the prior art are not well suited for self-administered testing, and web implementation of a hearing test demands self-administration. One reason is because the listener can fake a threshold and pretend that they are better than they really are, and yes-no procedures are susceptible to user bias. The prior art tests that do not adaptively find a hearing threshold are crude screeners that do not provide significant information about the person's hearing loss. The prior art tests that adapt the stimulus based on user input, also use basic yes-no procedures. Thus the result is determined based on analysis of yes responses and no responses to a sequence of queries. See, e.g., ANSI S3.21-1978, "Methods for Manual Pure-Tone Threshold Audiometry," and the description of computer controlled Bekesy Audiometry in ANSI S3.6-1996, "Specification for Audiometers."

More sophisticated testing algorithms are known which use standardized psychological procedures which improve the reliability and repeatability of the hearing loss measure, but such algorithms have not been applied in uncontrolled environments, like the internet. See, Levitt H., "Transformed up-down methods in psychoacoustics," J Acoust Soc Am. February 1971;49(2):Suppl 2:467+; Edwards B W, Wakefield G H. "Small sample statistical analysis of Levitt's adaptive psychophysical procedure," J Acoust Soc Am 1988 Apr 85, S 1:121; Schlauch R S, Rose R M. "Two-, three-, and four-interval forced-choice staircase procedures: estimator bias and efficiency," J Acoust Soc Am. August 1990;88(2):732–40; Green D., "A maximum-likelihood method for estimating thresholds in a yes-no task," J Acoust Soc Am., April 1993, 93: 2096–2105; and Green D., "Maximum-likelihood procedures and the inattentive observer," J Acoust Soc Am. June 1995;97(6):3749–60.

As the Internet gains popularity, and more individuals obtain the general-purpose processing power of personal computers coupled to the Internet and having sound cards or other audio processing capability, the Internet is becoming a more important medium for the delivery of audio products. Accordingly, it is desirable to leverage the communication technology the Internet used in the delivery of audio products for the purposes of performing hearing assessments in the home.

SUMMARY OF THE INVENTION

The present invention provides a technique allowing a web site visitor, or other user of a consumer electronic device that is remote from a hearing test server, to measure their hearing loss in an efficient and consistent way which is self-administered, and to store the measurements as a hearing profile which can be used for customizing audio products.

In one embodiment, the invention is a method for conducting a hearing test using a computer program. The method includes establishing a communication channel between a remote device and server in a communication network. A first component of the computer program is executed on the server, and a second component of the computer program is executed at the remote device. The computer program according to the invention comprises a routine to manage interaction via an interface on the remote device, and adaptively select stimuli based upon said interaction to be produced at the remote device according to a convergent process to determine a hearing characteristic. The interaction comprises an N-alternative forced choice interaction in one embodiment. The convergent, adaptive process comprises a staircase function or a maximum likelihood function in alternative embodiments of the invention.

In one embodiment, the routine to manage the interaction includes a process that causes a visual effect, such as displaying a graphic construct on a web page at the remote device, which corresponds to each of N alternative stimulus intervals, causes generation of a selected audio stimulus during one of the N alternative stimulus intervals, and prompts the test subject to make a choice by selecting a visual effect indicating the user's perception of the stimulus during the chosen one of said N alternative stimulus intervals. In various embodiments, the number N falls in the range of 2–4, for example.

In combination with the interaction procedure, a convergent, adaptive tracking process is provided for the purposes of selecting the stimulus to be presented during test. In one embodiment, the convergent process comprises selecting an initial audio stimulus in response to a baseline threshold which has been established for a remote device, producing a subsequent stimulus that is reduced in magnitude by a step down amount if the response in the interaction identifies a correct interval a number X times, or causing the device to generate stimulus that is increased in magnitude by a step up amount if the response in the interaction identifies an incorrect interval a number Y times. In one embodiment, the number X is 3 and a number Y is 1, for a 3 down, one up process. Preferably, the number X is in the range of 2–6, and the number Y is in the range of 1–4. However, these parameters of selected based upon the characteristics are the test executed.

In another embodiment, the convergent adaptive tracking process further includes a technique for adjusting the step up and step down amounts. Thus, in one embodiment after a number A of reversals of direction of the step direction, the process produces a subsequent stimulus that is reduced in magnitude by second downward step amount if the response in interaction identifies a correct interval a number X times, or produces a subsequent stimulus that is increased in magnitude by second upward step amount if the response in the interaction identifies an incorrect interval a number Y times. In this embodiment, either one or both of second downward step amount is less than the first downward step amount, and the second upward step amount is less than the first upward step amount.

According to various embodiments of the present invention, the remote device communicates with the server via a packet switched network, such as the Internet, which may establish links via wired or wireless communication media. Also, the remote device may communicate with the server via a cellular telephone network, a pager network, or any of a variety of communication technologies.

Also, according to various embodiments of present invention, the remote device comprises a mobile phone, a home computer, a hand-held computing platform, or other consumer electronics devices, such as home stereo or television equipment.

The present invention also provides an apparatus that comprises a data processor, a communication interface and memory which stores instructions in a form readable and executable by the data processor. The instructions specify processes which establish a communication channel with a remote device via the communication interface, and manage presentation of interaction with the test subject via an interface on the remote device, while adaptively selecting stimuli based on said interaction to be produced at the remote device according to a convergent process to determine a hearing characteristic. The data processor in this embodiment of the invention acts as a server which manages hearing tests remotely, enabling test subjects to self administer the tests using a variety of consumer electronic devices. In one embodiment, the apparatus comprises routines for downloading software components to the remote device for use during the interaction.

In yet another embodiment, the present invention provides a method for remotely testing hearing using a consumer electronics device which has a communication interface, an audio stimulus generator and an input device. The process includes remotely establishing a baseline threshold for a control signal supplied via the communication device which causes the device to generate a sound. Also, the process involves remotely managing an N-alternative forced choice stimulus and response interaction with the test subject. Also, the method includes adaptively producing signals to produce selected stimuli at the remote device for said interaction according to the convergent process that is based upon said baseline threshold and said interaction to determine a hearing characteristic.

Thus, the present invention enables remote, self-administered hearing tests managed using communication technology such as the Internet and a variety of consumer electronics devices as a test terminal.

Other aspects and advantages of the present invention can be seen on review of the drawings, the detailed description, and the claims which follow.

DETAILED DESCRIPTION

A detailed description of the various embodiments of the present invention is provided with reference to FIGS. 1–24.

Figure 1:
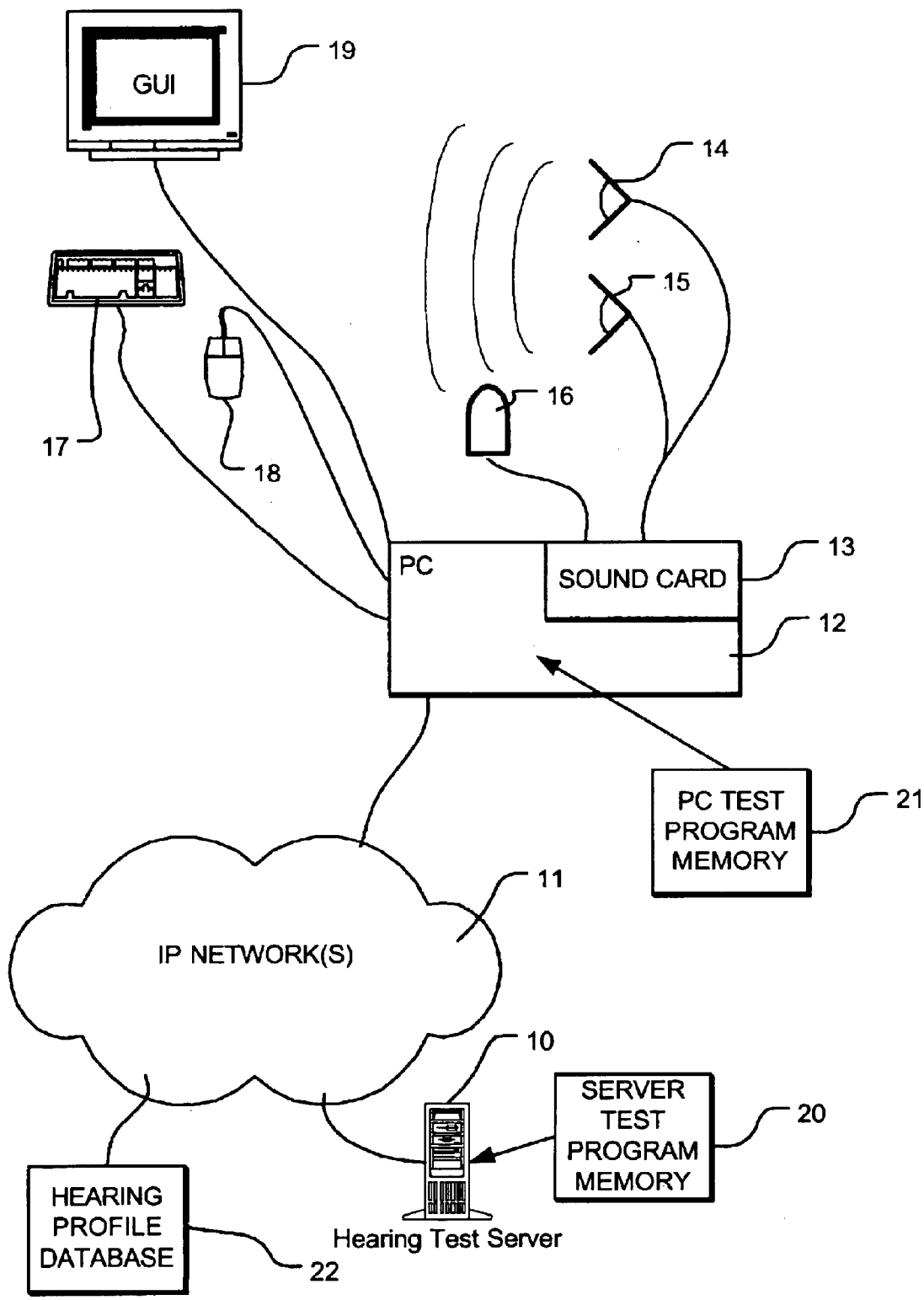
FIG. 1 illustrates an Internet based system for conducting a hearing assessment test according to the present invention.

FIG. 1 illustrates the Internet based system of the present invention implementing a hearing assessment test. System includes a hearing test server 10 coupled to a communication network 11, such as the Internet. The hearing test server 10 executes an interactive, converging hearing test protocol, such as the N-Alternative Forced Choice with a staircase convergence process described herein. A user end station 12, such as a personal computer, is also coupled to the communication network 11. The end station 12 includes a sound card 13 which provides data processing resources for producing audio output and receiving audio input under control of the logic in computer programs executed by the processor in the end station 12. In the figure, the sound card 13 is connected to stereo speakers 14 and 15, or to a headphone, and to a microphone 16. However, a wide variety of configurations exist in the end stations, which are not in the control of the hearing test server. The end station 12 also typically includes a display 19, a keyboard 17, and a mouse 18. During the test, audio stimuli in the form of sound signals produced in the sound card 13 are generated using the stereo speakers 14 and 15 in this example. The sound signals may be sampled or computed sound. Environmental factors such as background noise, and the level of the output of the speakers 14 and 15 could be sensed using a microphone 16. The display 19 is used to display a graphical user interface which prompts a user to input data using the keyboard 17 or the mouse 18 in response to the audio stimuli of the test.

The hearing test is executed using a computer program that includes a first component stored on the server test program memory 20 which is connected to the server 10, and a second component which is stored in the PC test program memory 21 which is connected to the end station 12. Upon completion of a test, a hearing profile is produced for the user. In a preferred system, this hearing profile is stored in a hearing profile database 22 which is accessible using Internet 11. In another embodiment, the hearing profile database 22 is coupled directly to the server 10. Alternatively, the hearing profile might be stored only on users end station and not made available to the communication network.

In this example, the end station 12 consists of a personal computer with standard s sound card components. In various embodiments, the end station consists of a mobile phone, a personal digital assistant, or other consumer electronic device, like home stereo or television equipment having the capability to communicate with a remote test server.

In one implementation, the hearing test server 10 maintains a web site. To initiate a hearing test, a user at the end station 12 accesses the web site and downloads a component (e.g. a web page with or without active code, a .wav file that encodes an audio stimulus, or other software component) of the hearing test computer program from the server 10 for execution at the end station 12. The user initiates the test without intervention by a third party, and uses the resources available via the Internet and the resources at the end station to conduct a hearing test.

Figure 2:
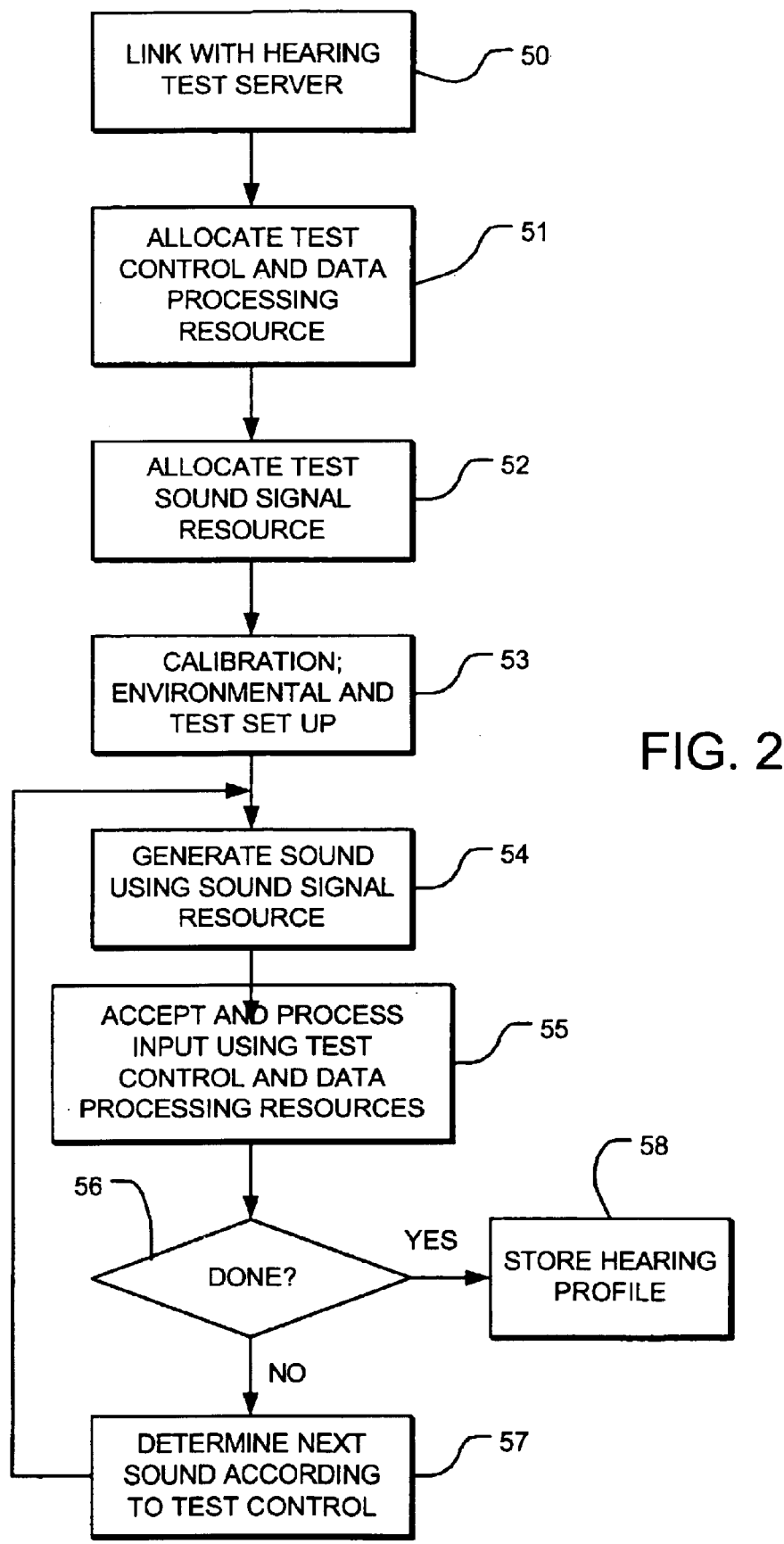
FIG. 2 is a flow chart illustrating the method of operation for an Internet based test according to present invention.

FIG. 2 illustrates the basic flowchart for the process of performing an Internet based hearing assessment test. In a first step 50, a user establishes a link between the end station and a hearing test server via a communication network such as the Internet. In one example, the link comprises a connection according to the transmission control protocol executing over the Internet protocol TCP/IP. The link may also involve protocols like the hypertext throughput protocol HTTP, and other Internet protocols. The link may be a wireless link via a cellular telephone network or a pager network.

In a next step 51, test control resources and data processing resources that will be utilized during the test are allocated. The allocation of these resources can take a variety of configurations, including maintaining all of the resources at the server, and providing an Internet based interface accessible using a browser or email client at the end station, maintaining the test control resources at the Internet server, and data processing resources at the end station, or other combinations as suits the particular implementation of the program to control the test and to process the data generated during the test.

In step 52, test sound signal resources are allocated. The sound signal resources may include sound samples, programs for generating sounds, or other common sound synthesis tools. The sound signal resources are adapted to the particular type of hearing test to be executed. In one embodiment, the sound signal resources are downloaded to the end station from the server. In another embodiment, the sound signal resources are available in the personal computer sound card without requiring download from the server, such as by providing recorded audio files with drivers for sound cards that are loaded on a user's end station. In another embodiment, sound signal resources are distributed between the end station and a server during execution of the test.

Next, optionally calibration programs are executed to evaluate the test environment (the audio environment in which the end station is situated), and the test set up (the audio characteristics of the equipment at the end station) to provide a baseline signal level for the device (step 53).

Upon completion of the allocation of data processing resources and calibration, test control resources and sound signal resources necessary for supporting the test, the test is initiated. The first step in the test is present an interactive interface to the test subject, including visual effects in N intervals, and to generate a sound using the sound signal resource in at least one of the intervals (block 54). Next, the process accepts and processes input using the test control and test data processing resources, by which the test subject signals a response selecting one of the N intervals as the one meeting the test criteria, such as whether the test subject heard the sound in this interval (block 55). Next the routine determines whether the test has been completed, applying statistical analysis of the responses which indicate convergence on a result (block 56). If the test is not completed, then the algorithm determines a next sound according to a convergent test protocol (such as a "staircase protocol") using the test control resources, in response to the input from the user and the state of the test (block 57). Then, the process loops back to step 54 to generate the next sound. If at block 56, it is determined that the test is completed, then the hearing profile is stored (block 58).

There are numerous options for prompting feedback from a test subjects. Options include accepting input in the form of the keystroke, a mouse click, use of a selection button or a timeout interval as volume is adjusted by the test control resources, or by the test subject action of increasing the volume, until some criterion is reached. A second option for accepting input includes causing the user to complete an action prompted by the graphical user interface, including graphical constructs which indicate respective test intervals, when test generated sounds meet some criterion during the respective intervals. For example, the test sound may be a sound varying in loudness. The test subject enters a mouse click when the sound disappears, or if it disappears in one of the N intervals. In another example, the test sound is played in one interval and not in a next. The test subject indicates the interval in which the sound is heard.

The test control resources can be distributed between the server and the end station using an Internet link, or using an executable file downloaded from the server and run locally on the test subject's equipment, or any partitioning of control in between. By controlling the test flow, the program can provide expertise for measuring and evaluating the level of background noise, testing for variability in the data, and in general control the flow and pace of the test process according to a test protocol. Controlling the test flow has specific advantages toward maintaining test subject interest as the user can be prompted to provide appropriate feedback and responses.

In other embodiments, data collected during the test can be returned to the web site server as raw data, as completely analyzed result data such as a hearing profile, or as any combination of raw and processed data in between. In one embodiment, data is not returned to the web site server in all, but rather completely processed locally on the end station using resources downloaded partially or completely from the test server.

The sound signals used in the testing process are implemented in several alternative forms. The type of test signals used can have significant influence on the results of the test through a number of psychoacoustic effects. A large number of possible test signals are applicable to any of the implementations. Examples of the types of test tones claimed are:

Pure tones of long duration and constant intensity in each test step utilizing a number of different test steps at different frequencies.

Pulses of pure tones and constant intensity in each step utilizing a number of different test steps at different frequencies.

Combination of tones of long duration and varying intensity in each test step utilizing a number of different test steps at different frequencies.

Pulses of combinations of tones and varying intensity in each step utilizing a number of different test steps at different frequencies.

Constant amplitude, swept frequency sound in each test step utilizing different test steps at different amplitudes.

Constant amplitude pulses of swept frequency sound in each test step utilizing different test steps at different amplitudes.

Bandpass filtered noise combined with test signals.

Speech sound with and without noise background with or without temporal compression or elongation.

Furthermore the method of test sound signal generation is not limited, and can include sampling using standard formats like MIDI, FM synthesis, wavetable synthesis or other sound generation techniques.

As mentioned before, a wide variety of hearing test protocols can be utilized for producing a hearing assessment. The particular test chosen depends on a variety of factors, including the use to which the hearing profile will be put, the type of equipment used at the end station, and any information about the physiology of the test subject which may affect the choice of hearing test. Example test types include:

1) Hearing Threshold Level.

The hearing threshold level test is related to identifying the sound level when the test subject can just begin to hear the test signal. This test type may be associated with determining that actual sound pressure level SPL of thresholds across the frequency range or the test method be simply to establish the relative level of thresholds as a function of frequency.

2) Masking Threshold Level.

The masking threshold level identifies the test signal sound level when the test signal can be heard out of a masking signal. The masking threshold test protocol can be completed at a number of different baseline amplitudes to give an indication of recruitment. This method may have some advantages when there is some background noise at frequencies other than the test frequency.

3) Loudness Matching.

In a loudness matching method, the generated sound consists of two different frequencies. One frequency is considered a baseline and is constant throughout a test. The other sound, the test sound, has a variable frequency during the test. A measurement consists of determining the loudness of the test sound that matches loudness of the baseline sound as a function of frequency. The resulting measurements are used to generate an equal loudness curve. The difference between the equal loudness curve obtained here and the equal loudness curve for normal hearing populations gives the hearing loss assessment. This test protocol can be completed at a number of different baseline amplitudes to give an indication of recruitment.

4) Loudness Growth in Octave Bands (LGOB).

Loudness Growth in Octave Bands is a subjective loudness evaluation procedure in which the test subject is prescribed set of common adjectives (e.g. very quiet, quiet, comfortable, loud, very loud and uncomfortably loud) to "measure" the loudness of test signals. The difference between the perceived loudness reported by the subject and a population of normally hearing individuals gives a measure of recruitment.

5) Speech Reception Threshold and Speech Discrimination in Noise or Quiet.

These test methods are based on the fact that different speech sounds have different frequency spectra and so the speech reception/discrimination capabilities of a subject are dependent on the subject hearing profile. Furthermore, noise can be used to test the breadth of the auditory filter. Tests with background noise are particularly interesting for internet administered test because the controlled noise level can be set to mask the environmental noise.

6) Temporal Masking.

Temporal masking of speech signals or tones can be used to probe auditory capabilities since it is known that temporal masking is affected by sensineural hearing impairment.

The test methods outlined above could be implemented in either a monaural or a binaural configuration. In the monaural implementation, each ear is tested individually and the other ear is "plugged" or otherwise deprived of test signal input. In an implementation scheme in which the headphones are supplied, the supplied headphones may have only one speaker. Clearly, there are advantages and disadvantages associated with either test method implementation with respect to accuracy and test complexity.

The basic test methods outlined above can be implemented within a number of different test configurations. The different test configurations may have different peripheral equipment, test protocols and they may have different levels of accuracy.

Figure 3:
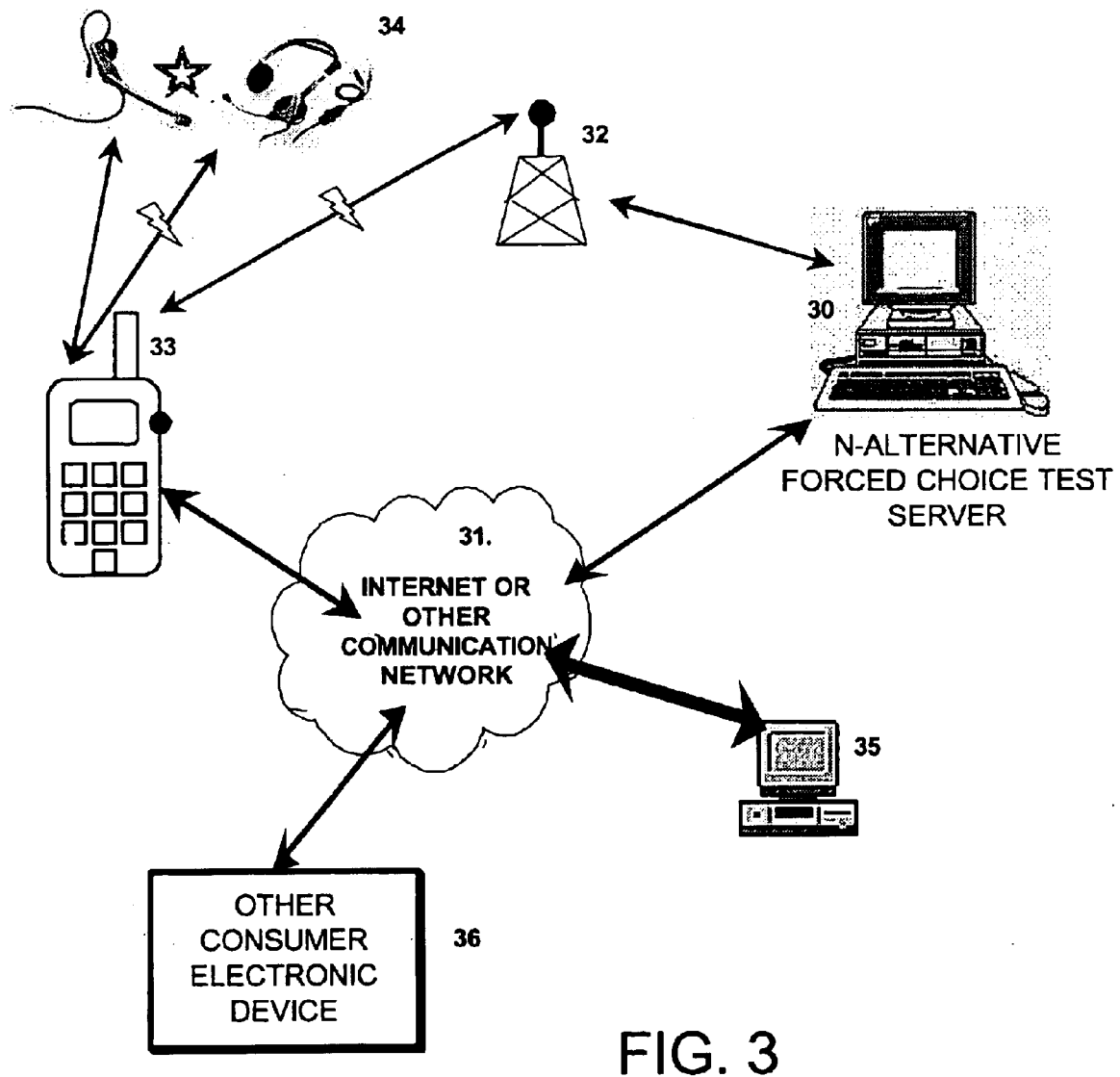
FIG. 3 provides a perspective of a variety of consumer electronic devices at which test subjects may take hearing tests according to the present invention.

FIG. 3 provides a perspective of a variety of other types of remote devices which are suitable for use as end stations for hearing tests according to the present invention. A hearing test server 30, configured in a preferred embodiment for an N-alternative forced choice test, is coupled to the Internet 31 or other communication network, and via a wireless link to a cellular station or other up link station 32 which may support for example a cellular telephone network or a pager network. Mobile phones 33 with or without peripheral devices 34 like headsets and microphones, communicate via the up link station 32 with the server 30. A personal computer 35 may be coupled via the Internet 31 to the server 30, and act as an end station for the test. Other consumer electronic devices 36, such as stereo equipment or televisions, which are equipped for interactive communication via the Internet 31 or other types of communication networks, are also used as end stations at which test subjects perform the hearing tests of the present invention.

According to one embodiment of the present invention, an N-Alternative Forced Choice Procedure is executed using an interactive interface on the consumer electronic device. Forced choice procedures eliminate user bias by forcing the listener to choose between right and wrong alternatives. With this, each trial consists of several successive intervals of sound or sound presentations. These sound intervals are usually associated with a visual cue that is presented during the sound presentation and a visual representation representing each individual sound interval. The listener then selects one of the N intervals according to the criterion that they have been instructed. For example, they may have been instructed to select the interval that has a tone, where the other N−1 intervals had no sound. Or they may have been instructed to select the one interval that is different from the other N−1 intervals.

Figure 4:
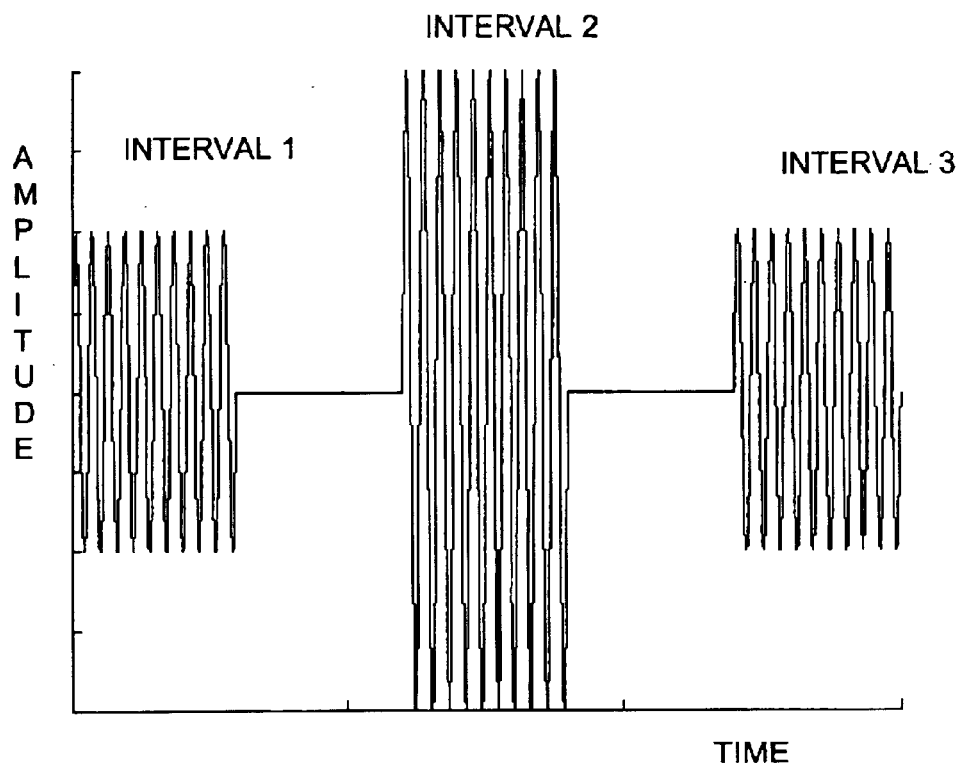
FIG. 4 illustrates signals generated for a three alternative forced choice step.
Figure 5:
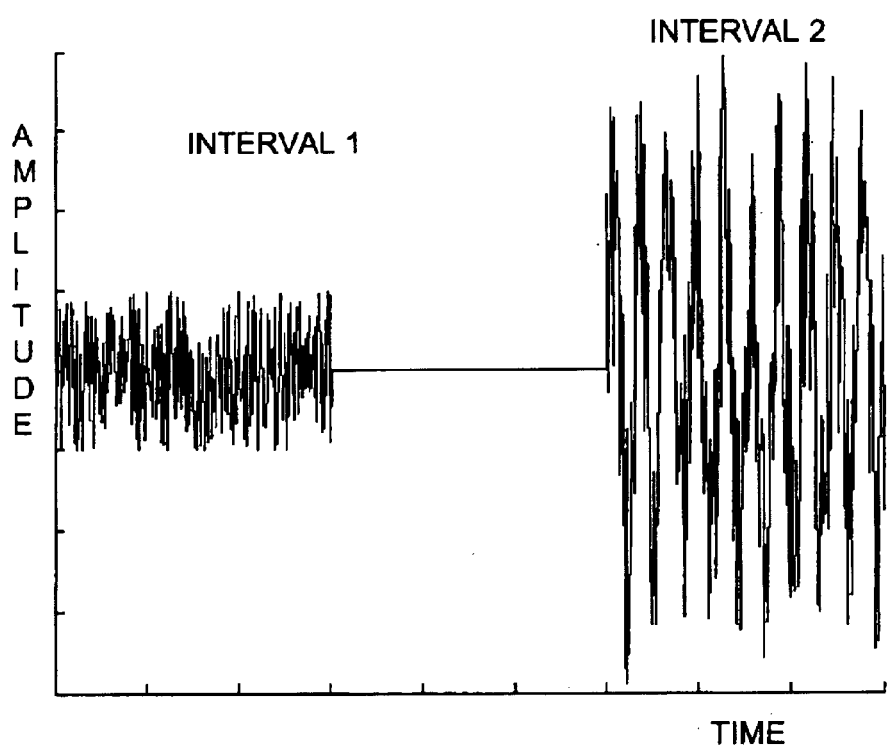
FIG. 5 illustrates signals generated for a two alternative forced choice step.

FIG. 4 is a plot of amplitude versus time, that shows tones produced for a 3-Interval Forced Choice where the listener is instructed to choose the interval that is different; here, the correct selection is Interval 2 which has a tone that is higher in level than the tones in Interval 1 or Interval 3. FIG. 5 is a plot of amplitude versus time, that shows tones produced for a 2-Alternative Forced Choice procedure where the listener has been instructed to select the interval which has a tone in the presence of noise; the correct answer is Interval 2, where Interval 1 has noise but no tone.

A convergent protocol for managing the test in one embodiment is an adaptive tracking procedure that meets accepted psychological standards. The adaptive tracking procedures described here are well known in the scientific auditory community but have not been used in web-based, or other remote hearing-loss measurement procedures. The first procedure, known as a staircase function, is an X-Down, Y-Up procedure where for every X incorrect responses, the task is made more difficult, and for every Y correct responses, the task is made easier. If the task is to detect a tone, X incorrect responses would result in an increase in the level of the tone for the next set of trials; Y correct responses would result in decreasing the level of the tone for the next responses. Both the correct and incorrect counts are reset to zero whenever the X or Y limit is reached. The method adaptively tracks to a specific percent-correct threshold, the value of which depends on the values of X and Y. For example, a 2-down, 1-up procedure adaptively finds the 70.7% correct point, while a 3-down, 1-up procedures finds the 79% correct point. This allows different thresholds to be estimated, depending on criterion such as number of trials wanted and performance level at which the user should hover around. The test continues either until a total number of trials has been reached or a total number of reversals has been reached. A reversal occurs for some tests when the adaptive procedure makes the test more difficult when the previous change had been to make the test easier, or when the test is made easier when the previous change was to make the test more difficult. For example, a reversal occurs when the adaptive procedure increases or decreases a sound level when the previous change had been in the opposite direction.

Figure 6:
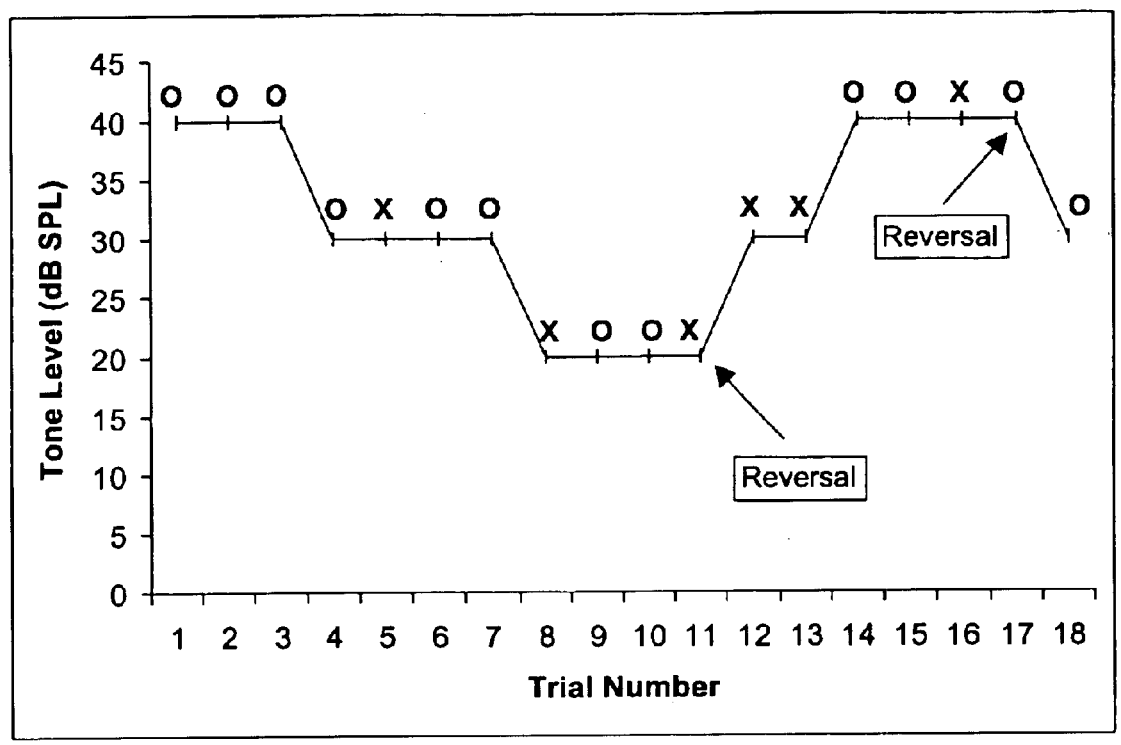
FIG. 6 illustrates a process flow for a convergent staircase procedure used with one embodiment of the present invention.

FIG. 6 is a plot of tone level versus trial number, that shows a run that used a 3-down, 2-up staircase procedure. Each symbol represents a trial where the listener had either a correct (O) or incorrect (X) decision. The abscissa indicates the trial number and the ordinate represents the level of the tone that is being adjusted according the listener. Table 1 details each trial of the run.

TABLE 1

| Trial # | Response | #Correct | #Incorrect | Change Level? Direction | Current Level | Next Level | Reversal? |
|---------|----------|----------|------------|-------------------------|---------------|------------|-----------|
| 1 | Correct | 1 | 0 | No | 40 | | |
| 2 | Correct | 2 | 0 | No | 40 | | |

TABLE 1-continued

| Trial # | Response | #Correct | #Incorrect | Change Level? Direction | Current Level | Next Level | Reversal? |
|---|---|---|---|---|---|---|---|
| 3 | Correct | 3 | 0 | Yes, Decrease | 40 | 30 | No |
| 4 | Correct | 1 | 0 | No | 30 | | |
| 5 | Incorrect | 1 | 1 | No | 30 | | |
| 6 | Correct | 2 | 1 | No | 30 | | |
| 7 | Correct | 3 | 1 | Yes, Decrease | 30 | 20 | No |
| 8 | Incorrect | 0 | 1 | No | 20 | | |
| 9 | Correct | 1 | 1 | No | 20 | | |
| 10 | Correct | 2 | 1 | No | 20 | | |
| 11 | Incorrect | 2 | 2 | Yes, Increase | 20 | 30 | Yes |
| 12 | Incorrect | 0 | 1 | No | 30 | | |
| 13 | Incorrect | 0 | 2 | Yes, Increase | 30 | 40 | No |
| 14 | Correct | 1 | 0 | No | 40 | | |
| 15 | Correct | 2 | 0 | No | 40 | | |
| 16 | Incorrect | 2 | 1 | No | 40 | | |
| 17 | Correct | 3 | 1 | Yes, Decrease | 40 | 30 | Yes |
| 18 | Correct | 1 | 0 | No | 30 | | |

An alternative to the up-down staircase tracking procedure is the maximum likelihood Procedure. See, Green, "Maximum likelihood procedures and the inattentive observer," J. Acoust. Soc. Am. 97(6), June 1995, pp.3749–3760. The maximum likelihood procedure assumes a form of the psychometric function (for example, percent correct as a function of the signal characteristic that is being adapted, such as level of a tone) and calculates the most likely psychometric function based on Bayesian statistics. There is the suggestion that this procedure is faster than an up-down procedure, but this is still being debated. This maximum likelihood procedure has also been applied to yes-know tasks in controlled environments.

Figure 7:
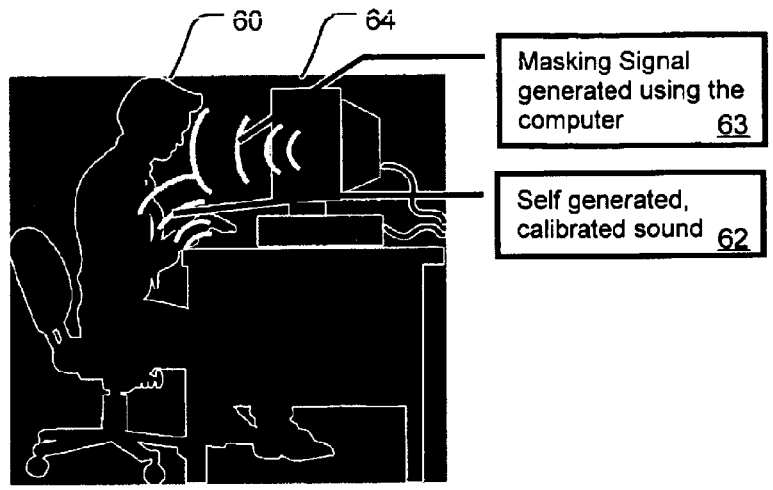
FIG. 7 illustrates a basic calibration set up used with one embodiment of the present invention.

A calibration module according to one embodiment "calibrates" a computer system sound card, or other audio resources at the consumer electronic device in a remote site. FIG. 7 shows the basic calibration concept according to a preferred embodiment. A test subject 60 at a remote device 64 produces a self-calibrated sound 62, while the audio resources are used to produce a masking signal 63. The calibration module is based on determining the computer mixer levels needed for a white noise signal to just mask (masking threshold) a calibration sound generated at the remote site by the test subject. Since the level of the noise generated at the remote site will be known within a range, the sound card mixer levels associated with the masking threshold will be understood to define a white noise sound pressure level within a range.

In this procedure, the system drives the mixer slider levels up until a user, through an input from the keyboard, indicates that the level of the masker has crossed through the masked threshold. Upon this input, the slider levels are automatically driven low, below the threshold level and subsequently back up toward a level slightly above the previous reversal. Again a user input indicating the threshold crossing, is used to halt the upward travel of the slider level. Multiple reversals are used to increase the accuracy of the estimate of the threshold.

The user will generate, using common items, a sound called the calibration sound (CS). From study of the noises generated, the range of the white noise levels needed to mask the sound will also be known. Examples of the specific noise generated, among many possible noises, include the following:

Striking the keyboard

Making circles on a piece of paper with a pencil

Rubbing two pieces of paper together.

The masker is, in one embodiment, a full band white noise (random numbers generated in the time domain). Throughout the calibration module, the presentation of the masker will be adjusted through adjustments made, for a personal computer running the Microsoft Windows operating system, to the All Wave slider and the Master Volume slider of the Windows Sound Card Mixer. These sliders will be adjusted simultaneously.

A masking sound of true, fullband white noise is generated through the generation of random numbers. The RMS power will be −5 dB bit. The relationship between dBpower and dBamplitude for white noise is:

$$dBpower = dBamplitude - 4.75\ dB$$

During the presentation of the masker, the presentation level of the masker will be modulated according to a predetermined algorithm that uses input from the user. The predetermined algorithm includes a ramp-up phase and a test phase. In the ramp-up phase the general region of slider position that corresponds to the masking threshold is determined and some protections are installed to ensure that the overall sound level can not get to maximum slider levels without direction from the user. In the test phase, the sliders are modulated from the reversal point, down below the threshold and then back through the threshold to 50% to 90%, for example, of the previous reversal value(s).

Figure 8:
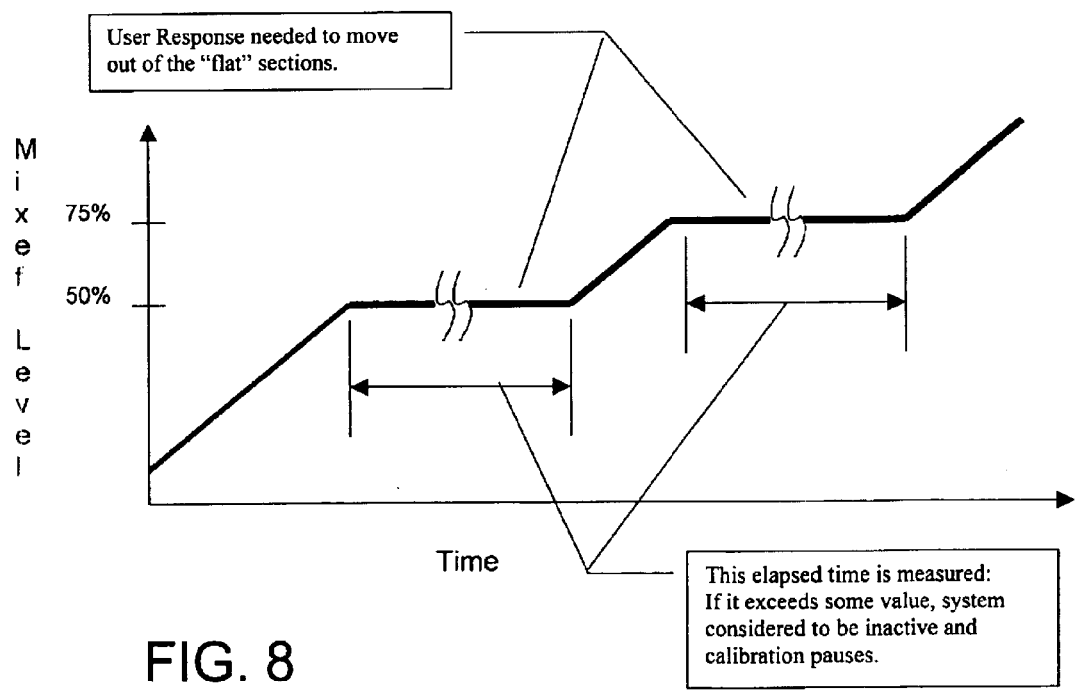
FIG. 8 is a plot showing mixer levels during the calibration procedure in one embodiment of the present invention.
Figure 9:
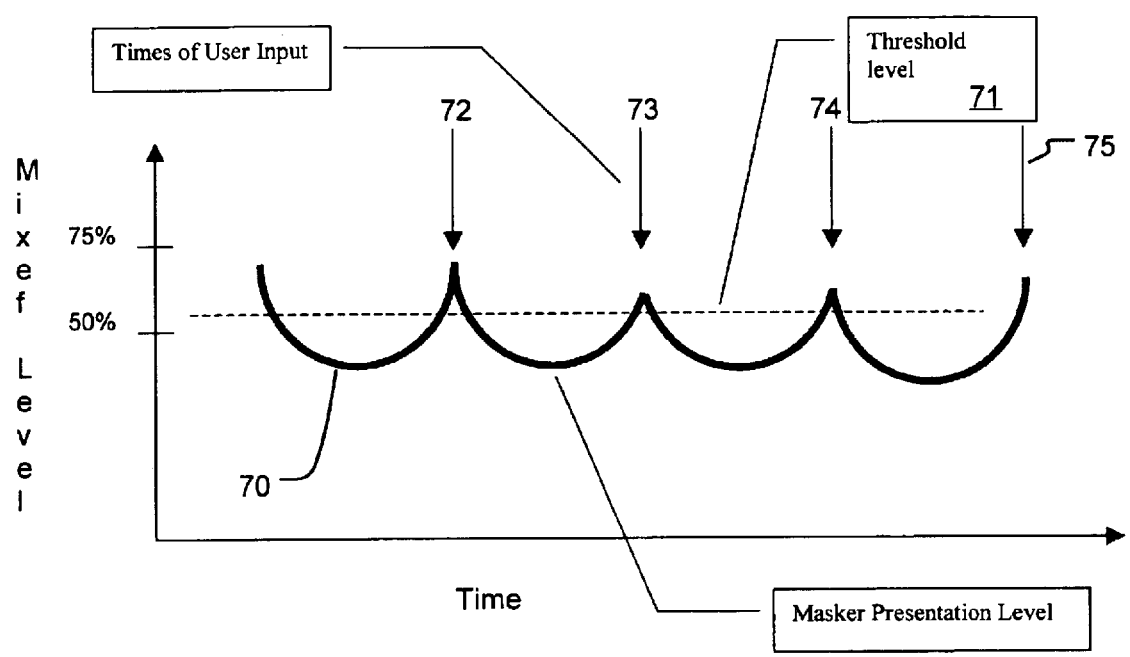
FIG. 9 is a plot showing management of signal levels during a calibration process in one embodiment of the present.

An effort to avoid allowing the mixer settings of a potentially loud system to be driven to their maximum values without user input, the ramp-up phase will include a number of regions where the level is not increased without further input from the user. FIG. 8 shows a schematic of the ramp-up phase. The various slopes and durations depend on particular configurations and design choices.

During the test phase, the mixer slider level automatically cycles from above the threshold to below the threshold to back above the threshold. A new cycle is initiated by the user input that indicates that the threshold has been crossed. FIG. 2 is a plot of a mixer level versus time, with a trace 70 of the masker sound level as it traverses a threshold level 71, and reverses after user inputs at times 72, 73, 74 and 75. Specific signal levels and slopes of the traces are determined based upon empirical analysis.

Embodiments of the present invention apply the principle of auditory masking as a basis for setting the output sound level of a remote system. Masking involves a determination of when the excitation pattern in the cochlea of the subject caused by the calibration sound is drowned out, or no longer sensed, because of the excitation pattern of the masking sound. Masking tests are superior to loudness based tests, more objective because the determination of whether the calibration sound can be sensed at all is more objective, and thus more repeatable, than a loudness comparison in which the subject is asked to state when two sounds have the same loudness. In the calibration method based on masking, the subject finds the masking level of a calibration sound, which is self-generated in some embodiments as described above, for a computer generated masking sound. In one embodiment, the calibration sound is generated by rubbing two sheets of paper together on a flat surface. This sound has good repeatability properties across individuals and locations. A masking sound spectrally shaped to match the calibration sound is preferred for the following reasons:

Reduced power at masker level. Some systems that previously were unable to output sufficient power to mask the calibration sound should now be capable of masking the calibration sound.

Reduce potential interactions between hearing loss and calibration sound spectral shape on the level set of calibration.

Another feature of the masking noise's spectral content is the affect speaker frequency response has on the actual dBSPL/Hz distribution expressed. Measurements indicate that the frequency response of typical speakers falls off somewhere above 4 khz. This speaker response can have implications on the variability of the resulting calibration since the masker level will need to be raised artificially high to mask the considerable high frequency energy present in the current calibration sound. In this situation, the response of the speakers will, in effect be setting the level of the calibration. As a result, it is advantageous to increase the spectral energy in the high frequency region so that the high frequency content of the calibration sound is masked, even in the face of speaker roll-off, long before the calibration sound components below about 4 khz.

The masking noise is a noise signal used to "drown out" the calibration sound. The masking noise is generated by the computer. The factors discussed above are included in defining the spectral shape of the masking signal, so that it matches the calibration sound to a degree sufficient for a reasonably accurate masking level test.

One embodiment of the spectral shape will be defined in terms of dB/Hz. Furthermore the spectral shape is specified in terms of normalized values since the overall level will be set by the subject. The spectral shape may be defined at a few frequency values. Linear interpolation of the dB/Hz values between the given values will be used to determine intermediary and limits. Smoothing of the resulting "shape" is not required. Values at or near DC are of little consequence since the output of typical computer sound systems at very low frequencies is attenuated. One example spectral shape is provided in the Table 2 below.

TABLE 2

Spectral Shape of Shaped Masker

| Frequency normalized | DC | 125 | 250 | 500 | 1K | 2K | 4K | 6.3K | 8K | 10K | 13K | 20K |
|---|---|---|---|---|---|---|---|---|---|---|---|---|
| dB/Hz normalized | <-80 dB | -18 | -18 | -18 | -12 | -6 | 0 | 0 | 0 | 0 | 10 | 10 |
| dB/Hz-MAX normalized | | -13 | -13 | -13 | -7 | -4.5 | 0 | 2.5 | 2.5 | 2.5 | 15 | 15 |
| dB/Hz-MIN | | -23 | -23 | -23 | -17 | -8.5 | 0 | -2.5 | -2.5 | -2.5 | 5 | 5 |

The phase of the signal may be essentially random across the + or − pi range.

As a result of the calibration process, the value of digital signals sent to the computer to produce a sound level near that of the calibration sound is determined. This value is expressed for example as dB down from a digital maximum level. Thus if the calibration sound is known to be about 68 dB, and the value determined by the masking process is about −45 dB, then a sound pressure level that is close to 40 dB will be produced by a digital value corresponding to −73 dB from digital maximum.

Figure 10A:
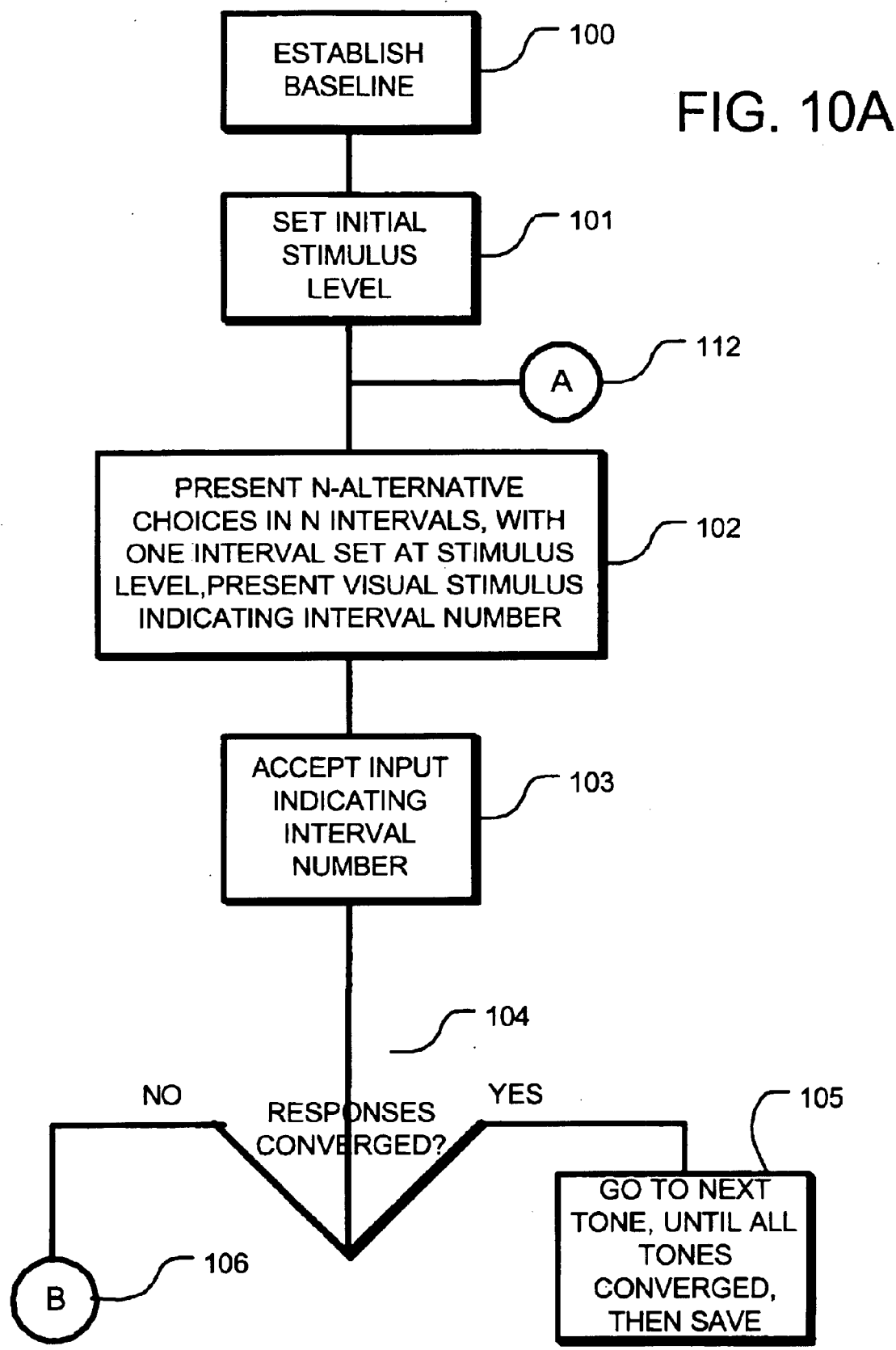
FIGS. 10A and 10B together provide a flow chart for a testing procedure in one embodiment of the present invention.
Figure 10B:
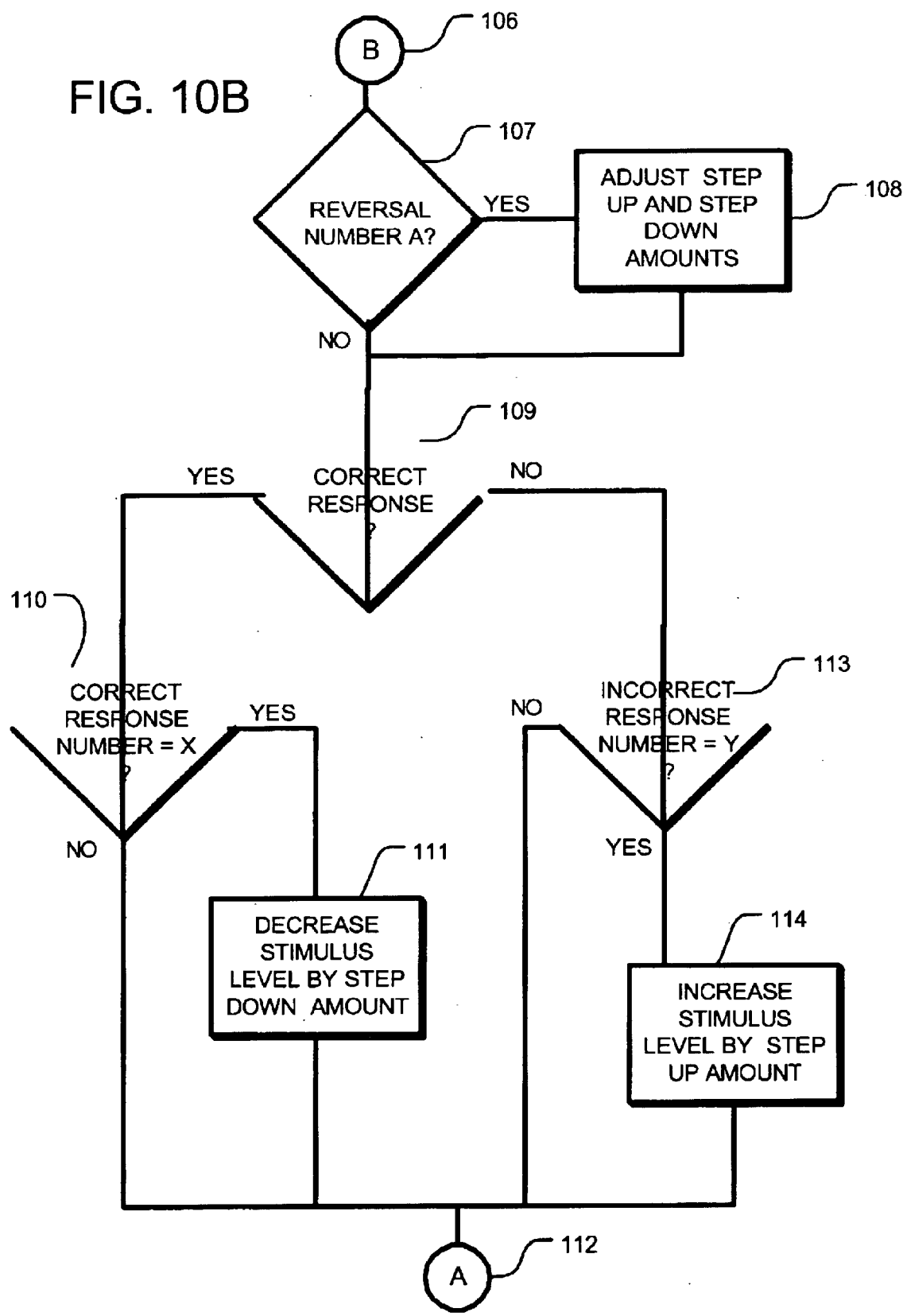

FIGS. 10A and 10B together show a simplified flow chart of one version of the interactive, converging test protocol of the present invention. The test protocol according to one embodiment of the present invention finds a hearing threshold level for a set of tones, such as 500 Hz, 1 kHz, 2 kHz and 4 kHz. It begins with a process to establish a baseline signal level for the remote device (block 100), using a calibration procedure, such as that described above, or other calibration procedures which may involve the use of specialized hardware or other techniques for direct measurement of sound pressure levels at remote device. Various calibration procedures are described in the above referenced related patent application Ser. No. 09/830,480, INTERNET BASED HEARING ASSESSMENT METHODS, invented by Menzel et al., filed Apr. 26, 2001, which is incorporated by reference as if fully set forth herein.

After establishing a baseline, the test resources set an initial stimulus level for a particular tone in the set of tones to be used in the test (block 101). The initial stimulus level may be for example about 30 dB above a typical hearing threshold for a normal hearing test subject. Next, N-alternative choices are presented in N time intervals, with one interval set according to the selected stimulus level, while at the same time presenting visual stimulus indicating an interval number to the test subject (block 102). The visual stimulus may be provided using a variety of techniques, such as Internet web page "button" constructs presented on a display at the remote device, or even simple lights on the remote device, such as LEDs on a mobile phone. The intervals last in one embodiment between 300 and 700 milliseconds, for example about 500 milliseconds. The time between the intervals is preferably less than a second, and more preferably about 300 to 700 milliseconds, such as for example, 500 milliseconds. According to the protocol, input from the test subject is accepted indicating the interval number during which the selected stimulus is perceived by the test subject (block 103). The process determines next whether the responses have reached a stopping criterion indicating convergence on a result, such as by determining a percent correct parameter (block 104). If the responses have converged, then the algorithm branches to block 105, where the it proceeds to the next tone until all the tones in the hearing test have converged, and the test results are saved. If at block 104, it is determined that the responses have not converged, the process proceeds through B (block 106) to the process of FIG. 10B. Next, the number of reversals is determined (block 107). If the reversal number matches a number A, then the step up and step down amounts are adjusted (block 108). If the reversal number is more or less than A, or after block 108, the process determines whether the test subject provided correct response (block 109). If the response was correct, then the process determines whether the number of correct responses matches X (block 110), if the number of correct responses matches X, then the stimulus level is decreased by a step down amount (e.g. down by 10 dB initially and 5 dB after the number A reversals have been encountered) and the correct response number is reset (block 111). If the correct response number is less than X, or after block 111, then the process loops through A (block 112) back to the process at block 102 of FIG. 10A. If at block 109, it is determined that the test subject did not provide a correct response, the algorithm determines whether the incorrect response number matches Y (block 113). If the incorrect response number matches Y, then the process increases the stimulus level by a step up amount (e.g., up by 10 dB initially and 5 dB after A reversals have been encountered), and the incorrect response number is reset (block 114). If the incorrect response number is more than or less than Y at block 113, or after block 114, the process loops through A (block 112) back to the process at block 102 of FIG. 10A.

The parameters A, X and Y in the process of FIGS. 10A and 10B can be selected as suits needs a particular testing environment, and of a particular hearing characteristic being tested. For a basic hearing profile, X equals a number in the range of 2 to 6, and Y equals the number in the range of 1 to 4. For example, the test where X equals 3, and Y equals 1 is useful, providing a "three down, one up" convergence process. The parameter A falls preferably in a range of 2 to 5 for a basic hearing profile.

In a preferred embodiment, the parameter X equals 1, and the parameter Y equals 1, until the first reversal. (One down, one up). Thereafter the parameter X is changed to 3, and the parameter Y remains 1. (Three down, one up). It is found that the initial one down, one up stage speeds the convergence process.

Also, the adjustment of the step up and step down amounts may be allowed to occur only once in a given test procedure, or may be allowed to occur many times as suits in the needs of a particular process.

As mentioned above, an alternative adaptive, converging process for adaptively selecting the stimulus levels, and converging on a result is the maximum likelihood test, in which a statistical process is applied to predict a next stimulus level based on a likely threshold determined from a set of responses gathered during the test. A single false or erroneous response does not cause the program to presume convergence for maximum likelihood algorithm.

Figure 11:
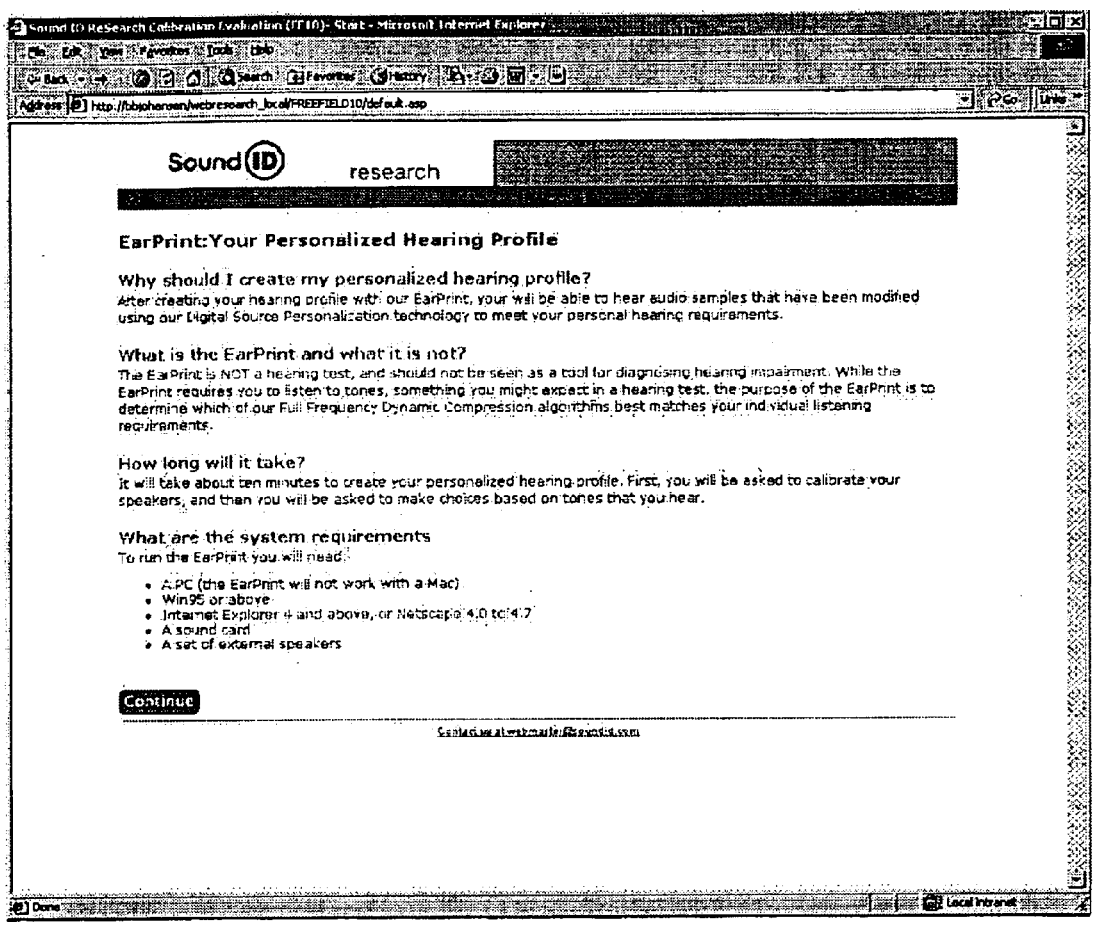
FIGS. 11–24 are images of web pages used for presentation of a hearing test according to one embodiment of the present invention.
Figure 12:
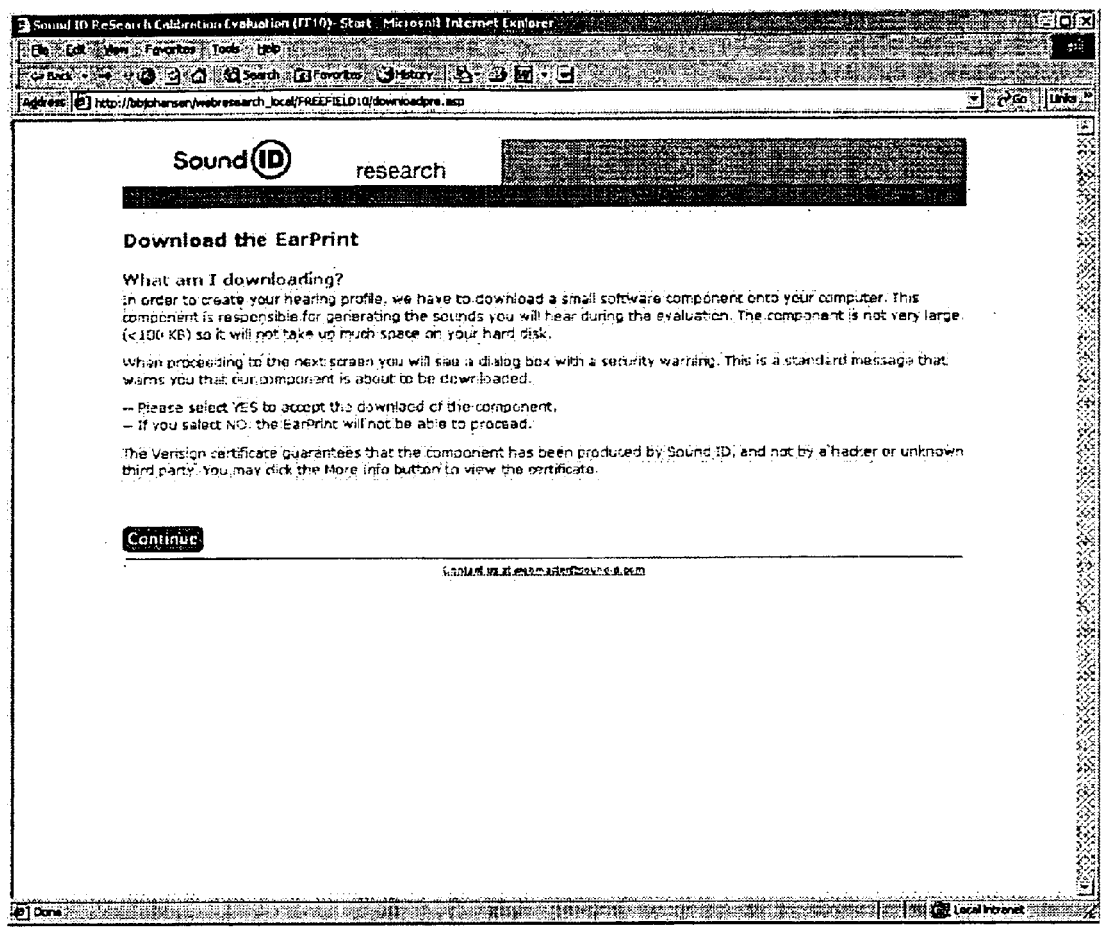

FIGS. 11 through 24 are images of web pages generated by a routine that causes presentation of an N-alternative forced choice hearing test providing interaction with a convergent procedure according to one embodiment of the invention. The web pages are rendered by a standard Internet browser, such as Internet Explorer provided by Microsoft Corp., in an interaction with the test server. An opening screen for this example is shown in FIG. 11. The opening screen of FIG. 11 introduces the concept of the hearing profile and explains system requirements to a test subject. If the test subject selects the "continue" button on the web page of FIG. 11, the page of FIG. 12 is presented, which prompts the test subject to allow downloading of a component of the hearing test program from the server for use in execution of the test. In this embodiment, the component downloaded comprises a routine, implemented for example as a DirectX file, for generating the audio stimulus for the test and calibration processes, for managing the interaction during the test and calibration processes, and for adaptively selecting the stimulus levels according to a staircase function as described above. The server continues to execute a component that maintains communication with the remote site, and reacts to messages from the remote site, such as receiving the results of the testing, and interacting with the test subject before and after the test.

Figure 13:
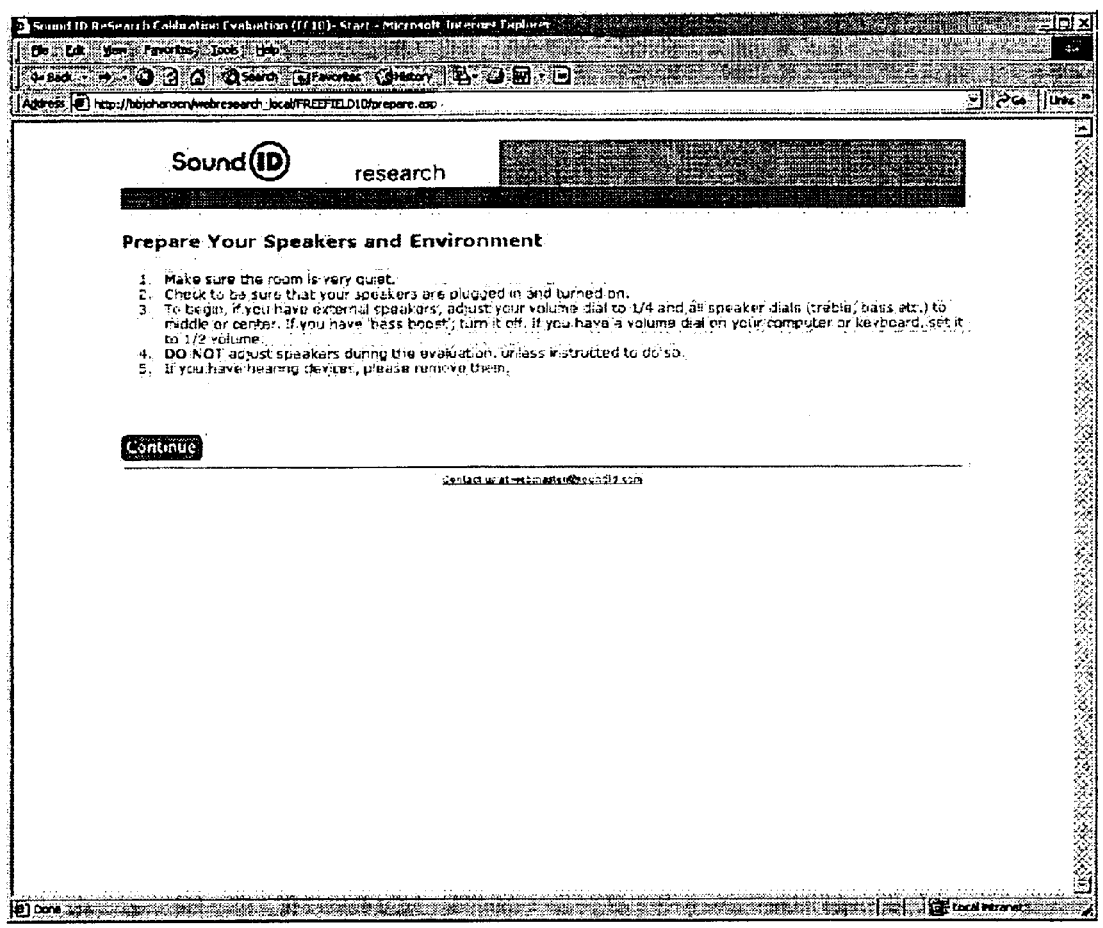

If the test subject selects the "continue" button on the web page of FIG. 12, then the component is downloaded, and the web page shown in FIG. 13 is presented. The web page of FIG. 13 prompts the user to prepare the speakers and environment for the test. This includes instructing the test subject to make adjustments of the audio parameters on the device, such as a personal computer, to be used during the test.

Figure 14:
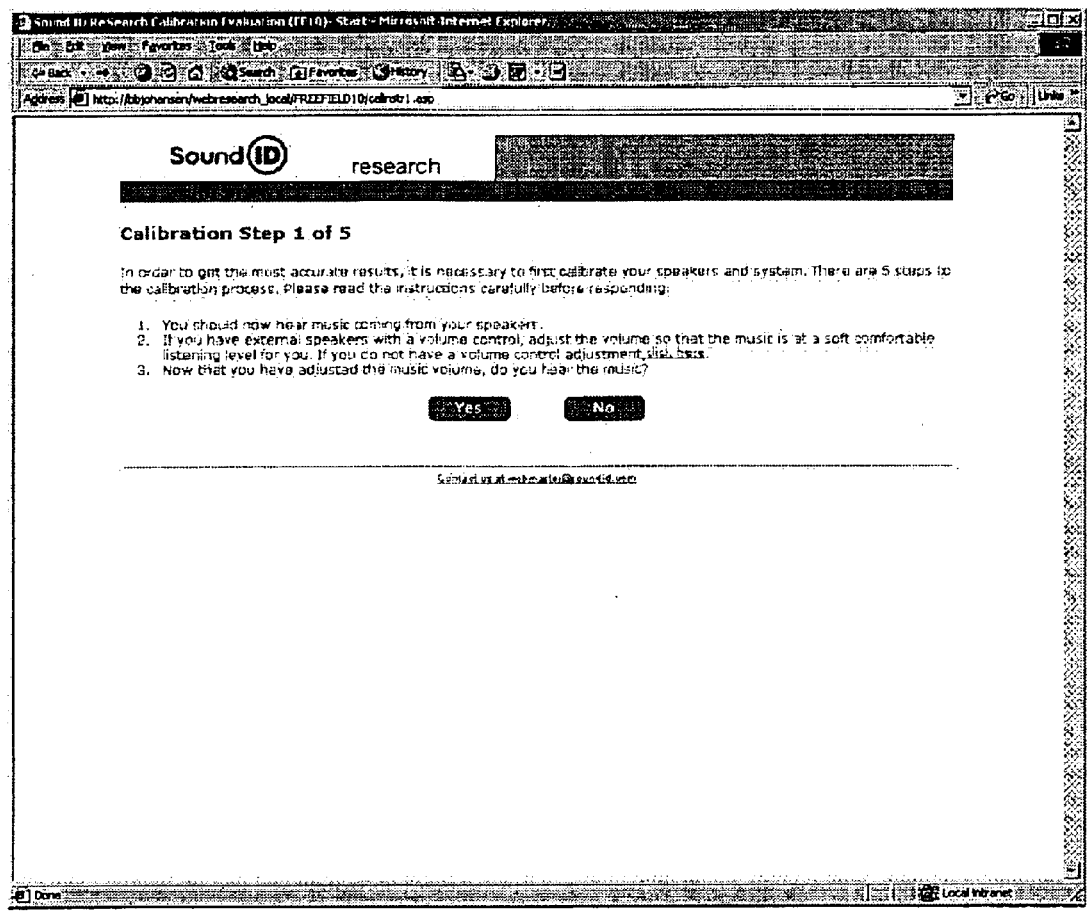

If the test subject selects the "continue" button on the web page of FIG. 13, message is shown to the user that a software component is being downloaded to support the calibration step. The component downloaded at this stage is a compressed audio file storing music. When the music file is downloaded, the web page shown in FIG. 14 is presented. The web page shown in FIG. 14 explains the first step in a calibration process. According to the first step, during presentation of the web page, the music file is played in the speakers. Users instructed to adjust the volume so the music is at a soft, comfortable listening level. If the user successfully performs this step, and selects the "yes" button in FIG. 14, then the web page shown in FIG. 15 is presented.

Figure 15:
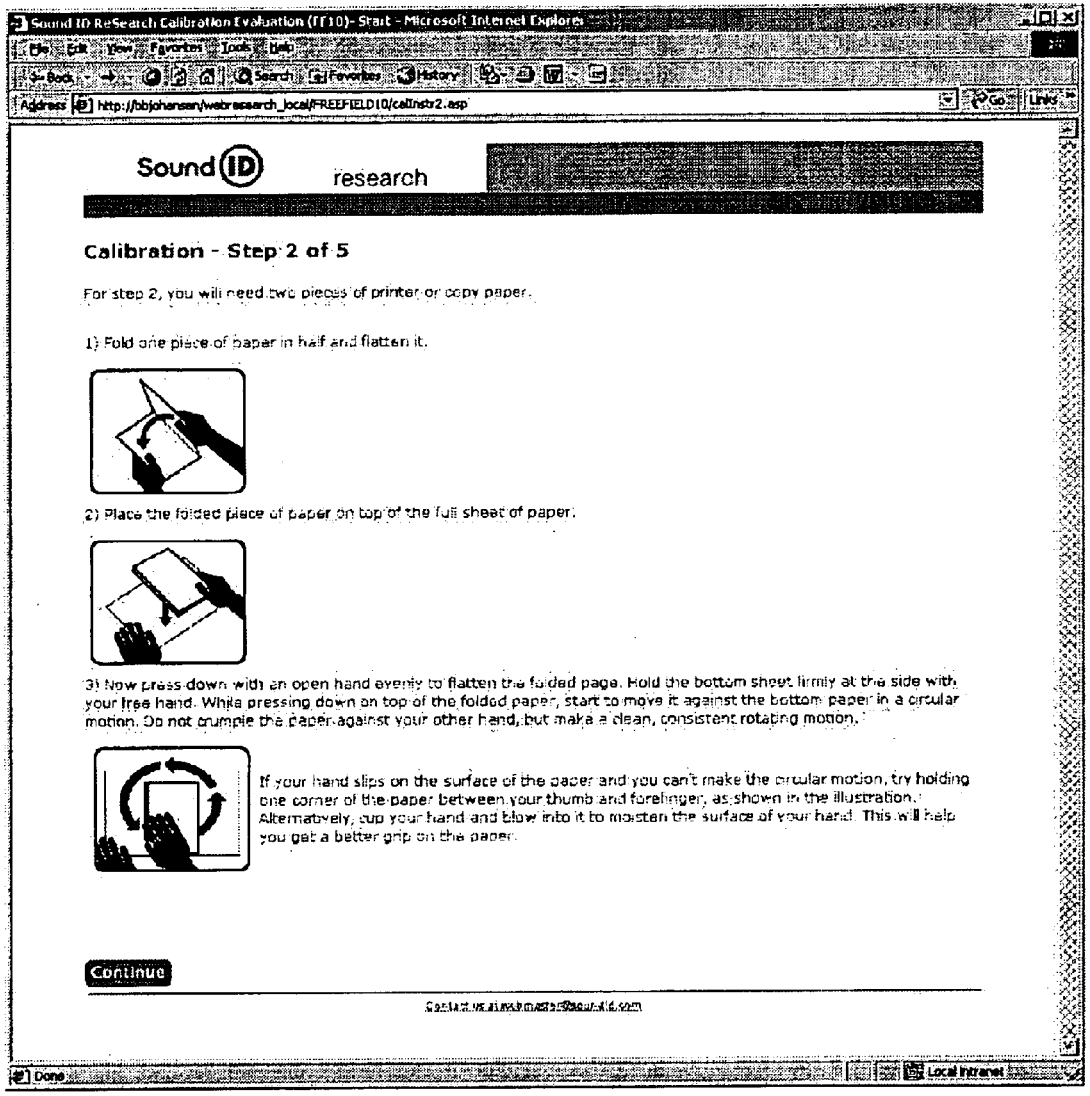

The web page shown in FIG. 15 explains the second step in the calibration process. During the second step, the test subject prepares a calibration sound source using ordinary items. In this example, the web page explains how to prepare to pieces of printer or copy paper so that the process of rubbing the paper together can be executed to generate a calibration sound. If the user presses the "continue" button on FIG. 15, then the web page shown in FIG. 16 is presented.

Figure 16:
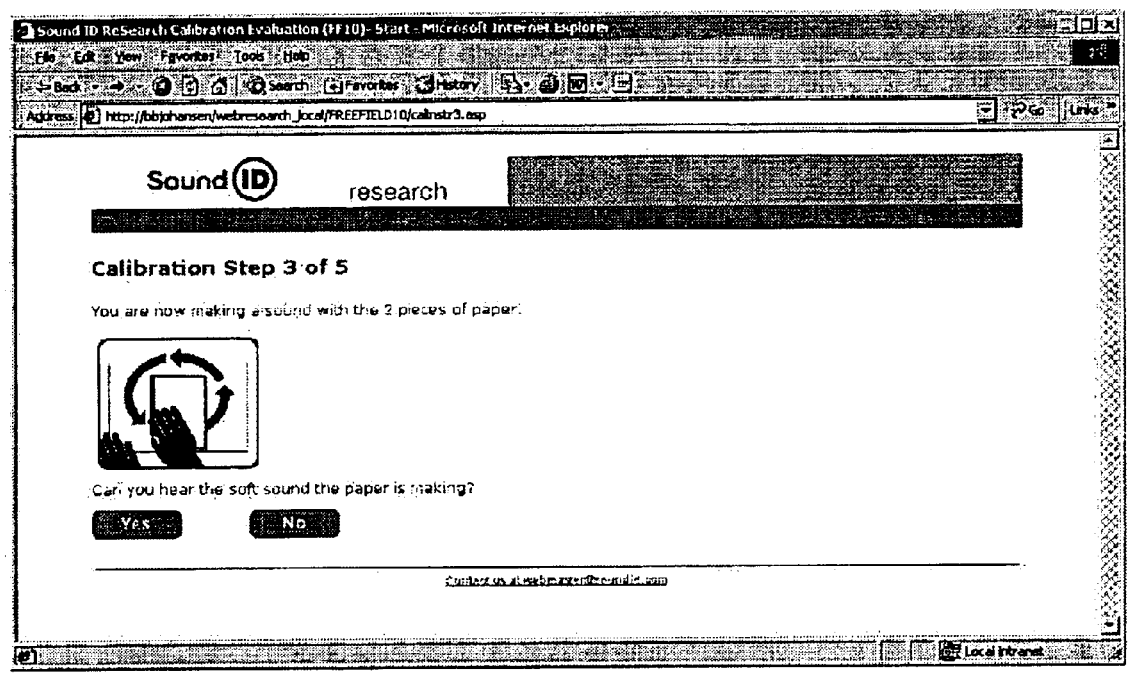

The web page shown in FIG. 16 prompts the test subject to verify that a calibration sound is being made using the items described in FIG. 15. If the test subject selects the "yes" button in the web page of FIG. 16, then the web page of FIG. 17 is presented.

Figure 17:
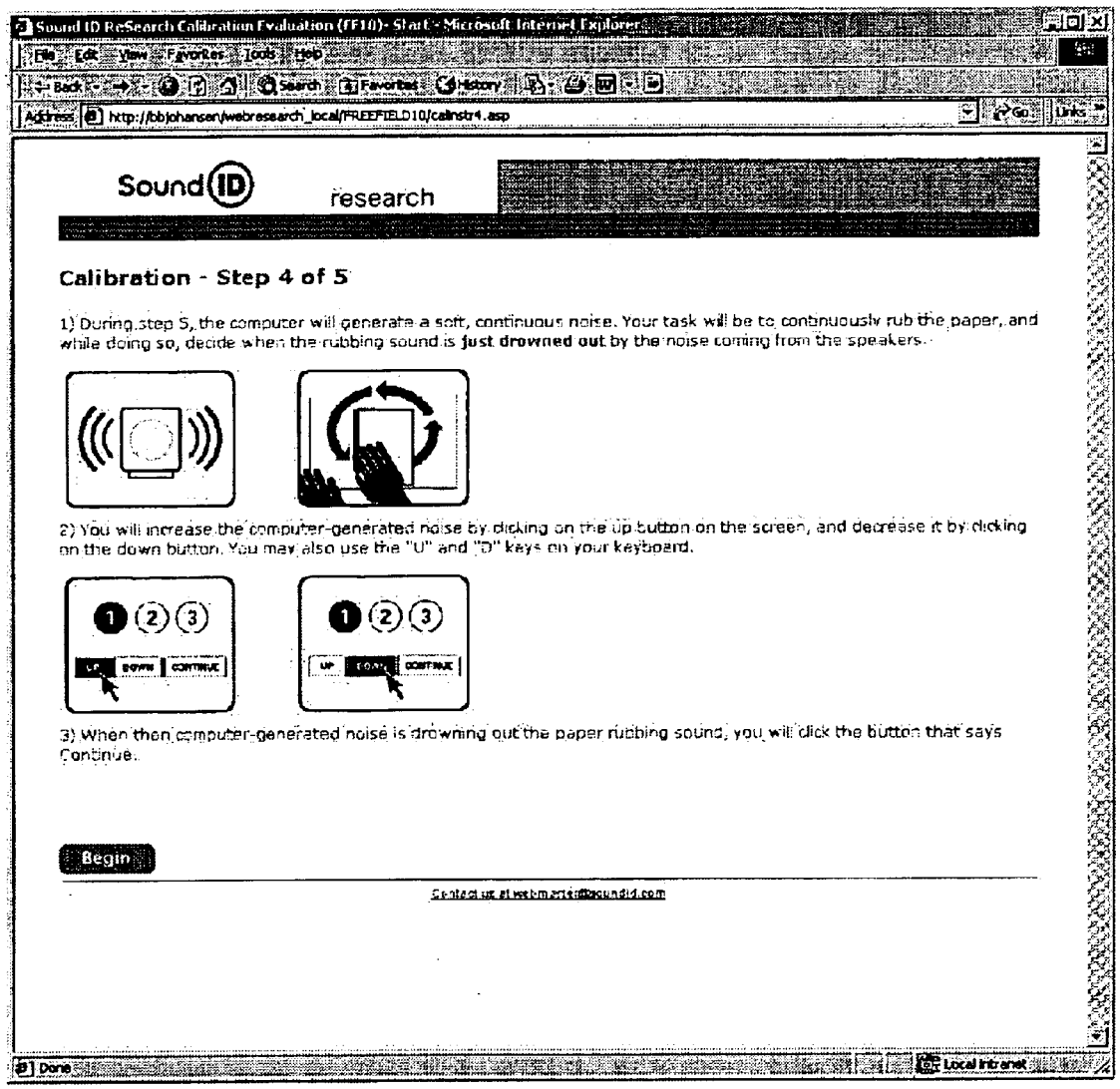

The web page of FIG. 17 illustrates and explains the process to be used in order to set a baseline level for the personal computer using the calibration process. Basically, the computer generates a soft, continuous noise. The test subject continuously rubs the paper together, and decides when the calibration sound is just drowned out by the noise coming from speakers. The test subject increases the computer-generated noise by clicking on a button in the screen presented during this process, or by using other input devices. Finally, the web page in FIG. 17 explains that when the computer-generated noise is drowning out the paper rubbing sound, then the test subject signals completion of the test by clicking the "continue" button to be presented during the test. If the user selects the "begin" button shown in FIG. 17, then the web page shown in FIG. 18 is presented.

Figure 18:
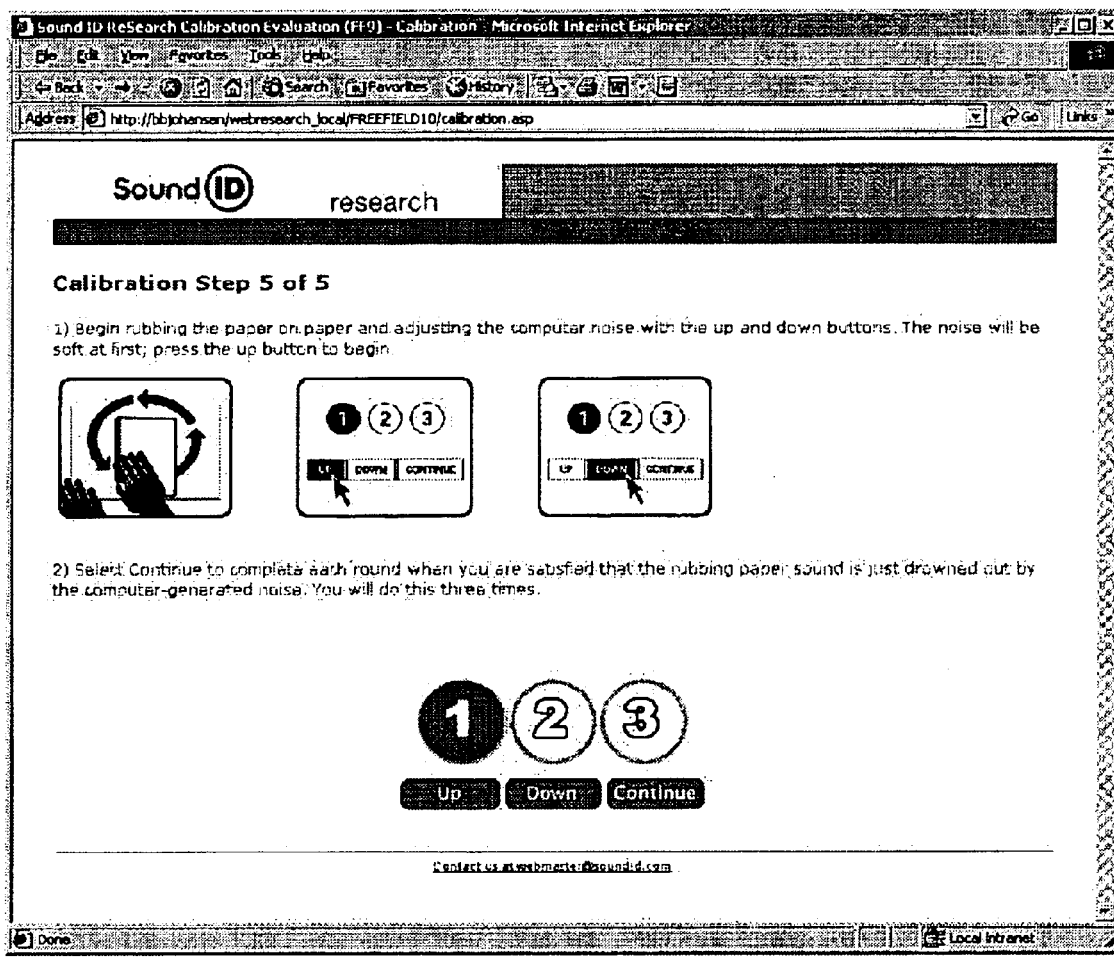

The web page shown in FIG. 18 is the last step in the calibration process, during which the test subject determines the level at which the computer-generated noise drowns out the paper rubbing sound. Thus, the web page shown in FIG. 18 prompts the user to begin rubbing on the paper and adjusting the computer-generated noise using the "up" button, and "down" button, until the masking level is reached. When the masking level is reached, then the user is instructed to select the "continue" button. The screen includes three indicators, which comprise the numerals 1, 2 and 3 within respective circles. When the test is completed a first time, the first indicator is highlighted. When the test is completed a second time, the second indicator is highlighted. When the test is completed the third and final time, the third indicator is highlighted. When the test subject selects the "continue" button after the third level setting process in the web page of FIG. 18, then the web page of FIG. 19 is presented.

Figure 19:
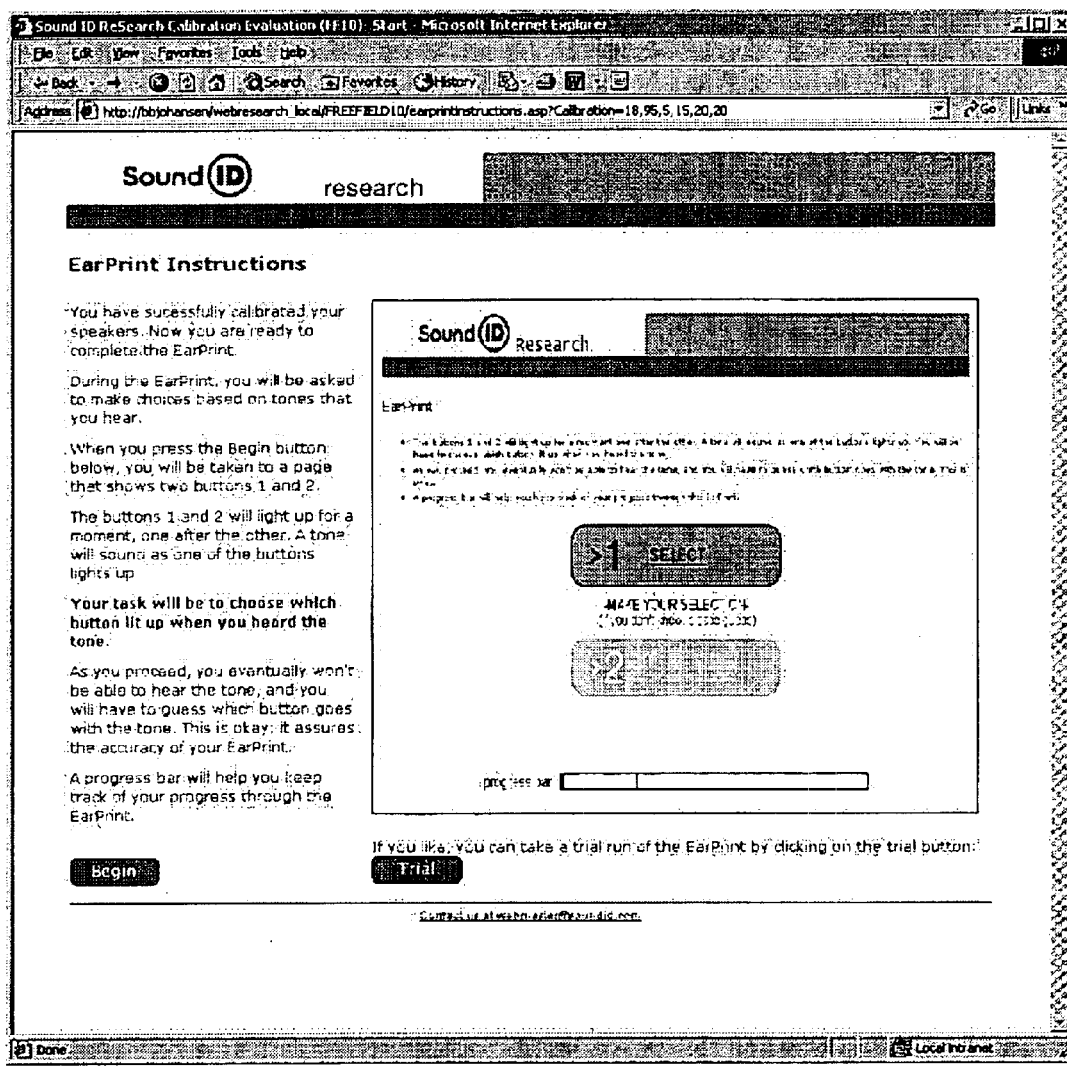
Figure 20:
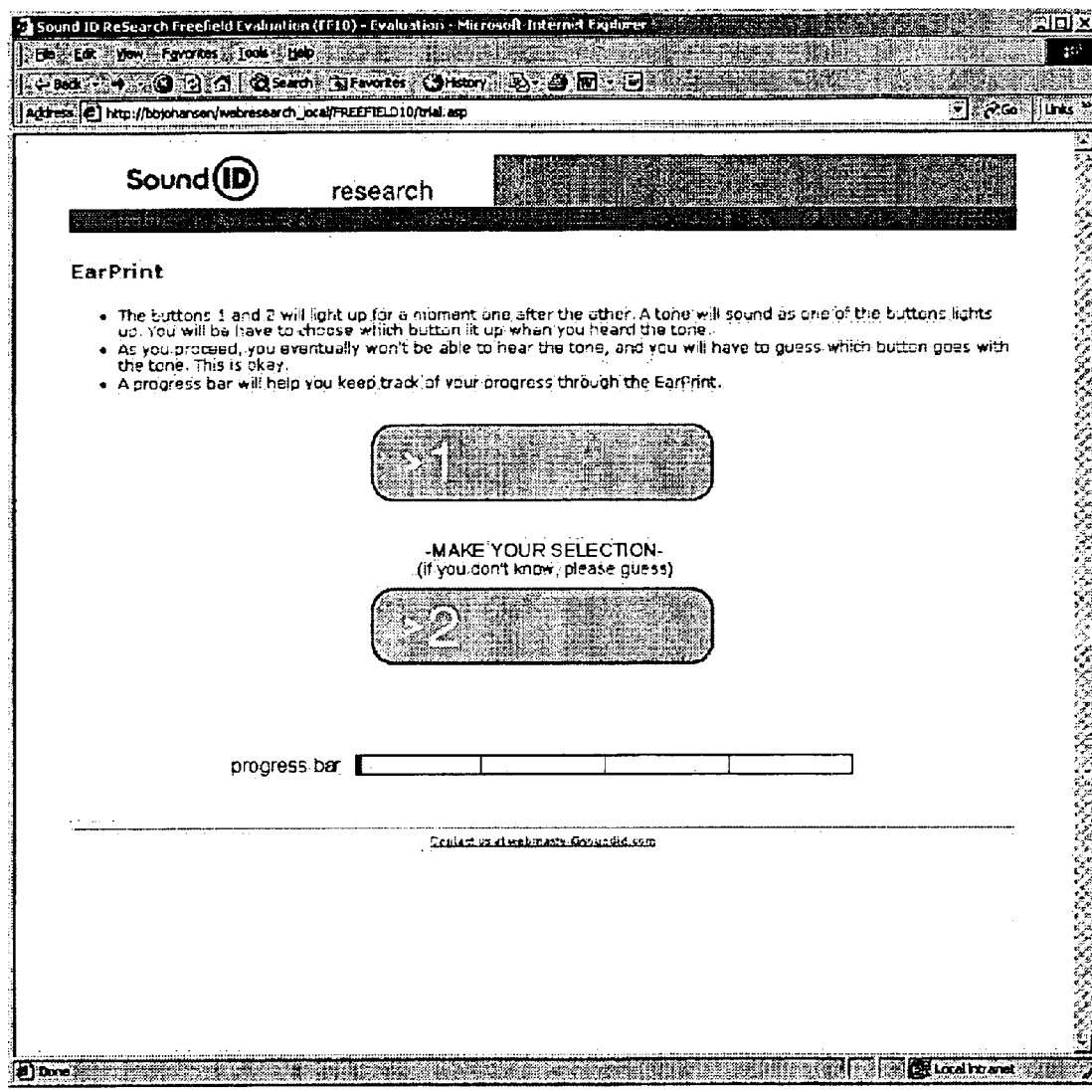

The web page of FIG. 19 represents the start of the N-alternative forced choice test, and explains that testing procedure. Thus, the web page of FIG. 19 explains that the test subject will be asked to make choices based on tones that he or she hears. In the example shown in FIG. 19, the test subject is offered the opportunity to run a trial by selecting the "trial" button in the web page of FIG. 19. If the user selects the "begin" button in the web page of FIG. 19, then the web page of FIG. 20 is presented. The buttons "1" and "2" in FIG. 20 will light up, or otherwise be highlighted, for a moment, one after the other. A tone will sound as one of the buttons lights up. The task of the test subject is to choose which button lit up when the tone was perceived. As the test subject proceeds, the test subject eventually will not be able to hear the tone and will have to guess which button goes with the tone. A progress bar keeps the test subject informed about progress of the testing. The buttons "1" and "2" are graphic constructs aligned in an up and down relationship, rather than a left and right relationship in this embodiment of the invention. It is found that the up and down relationship is preferred in environments in which test subjects may be mistakenly correlate the left button with a left speaker and the right button with a right speaker in a stereo configuration.

Using this interface, where the visual indicators of the test intervals comprise highlighting of the buttons "1" and "2," the user is prompted through the testing procedure. The testing procedure follows a process such as described above with respective FIGS. 10A–10B.

Figure 21:
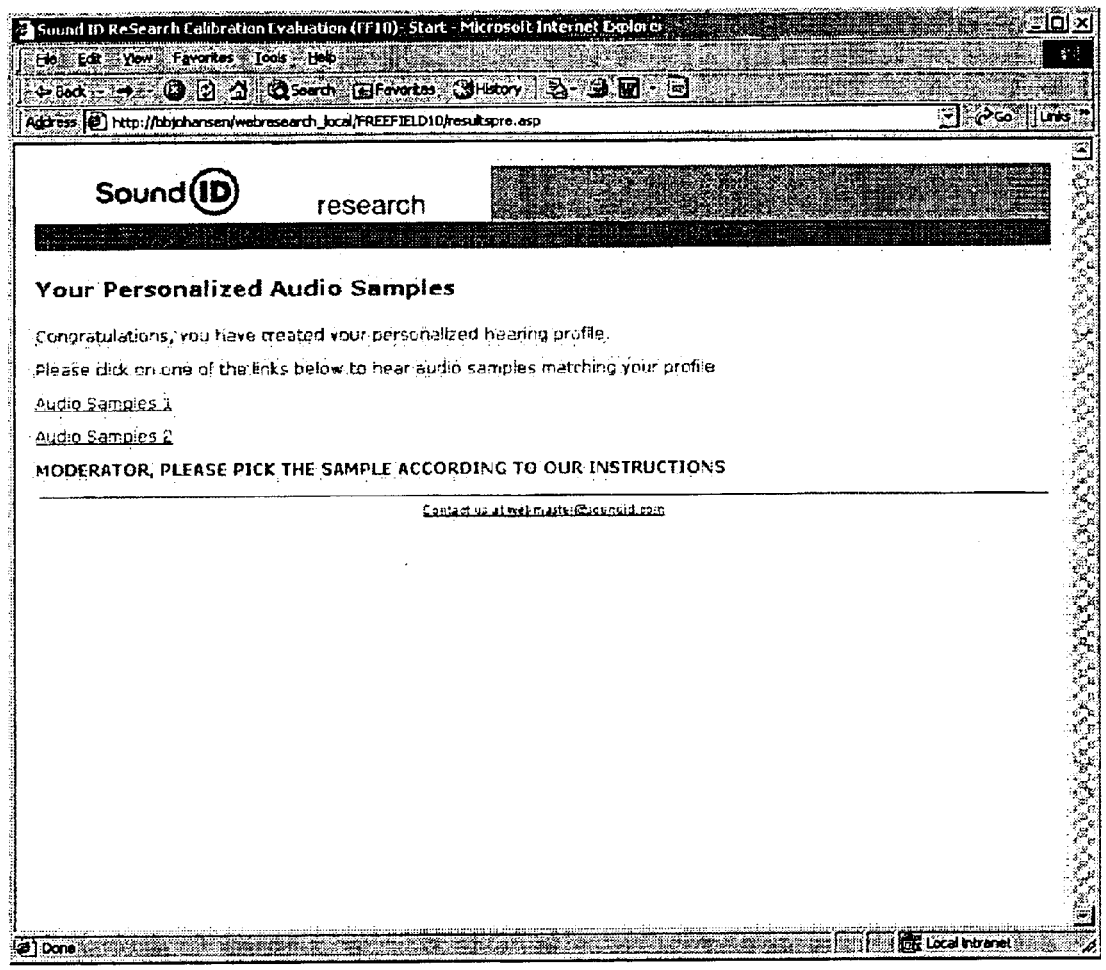
Figure 22:
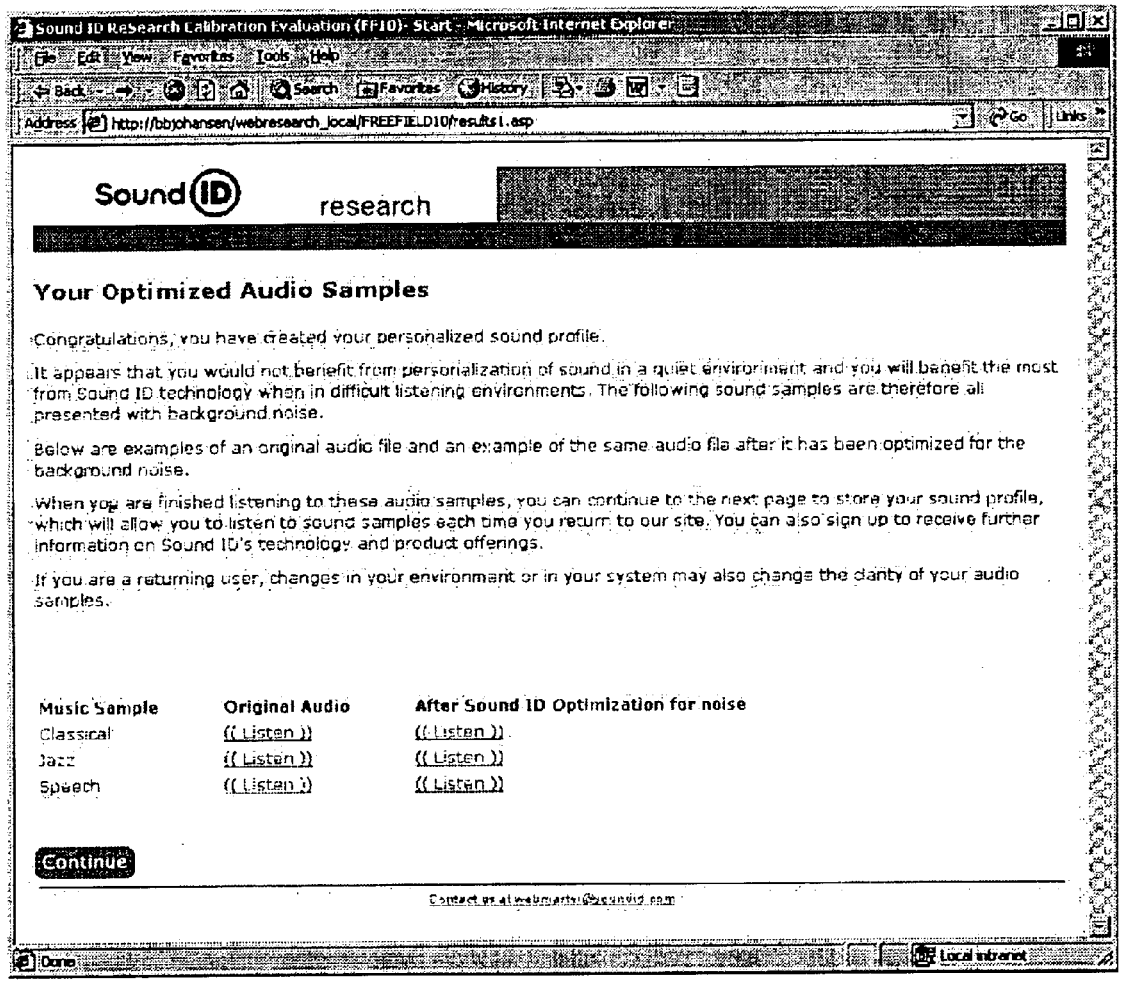

When the test is completed, either the web page shown in FIG. 21 or the web page shown in FIG. 22 is presented. The web page of FIG. 21 is presented if the hearing profile produced by the test suggests that the test subject could benefit from personalized audio generated by applying hearing profile. In the web page of FIG. 21, the test subject is prompted to playback audio samples which have been adapted according to the hearing profile created using the test. The web page of FIG. 22 is presented if the hearing profile of the test subject is within a normal range, suggesting that the hearing profile can be applied for personalized audio products in a noisy environment, but may not be necessary in a quiet environment. The user is prompted to select samples of audio products which simulate a noisy environment in a original format and in a optimized format.

Figure 23:
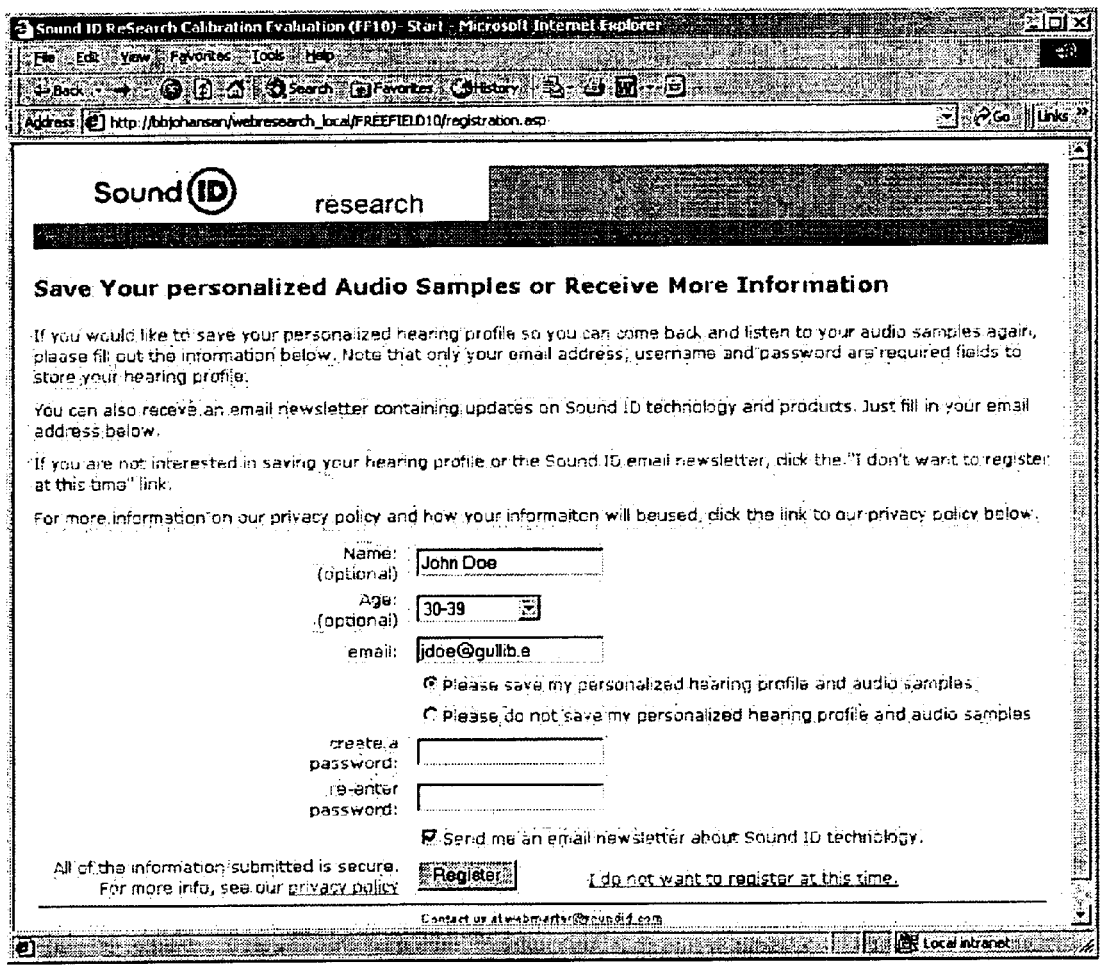

If the user selects the "continue" button in the web page of FIG. 22, then the web page of FIG. 23 is presented. The web page of FIG. 23 allows the user to register with the web site, store the hearing profile, and otherwise participate in activity supported for registered users of the web site.

Figure 24:
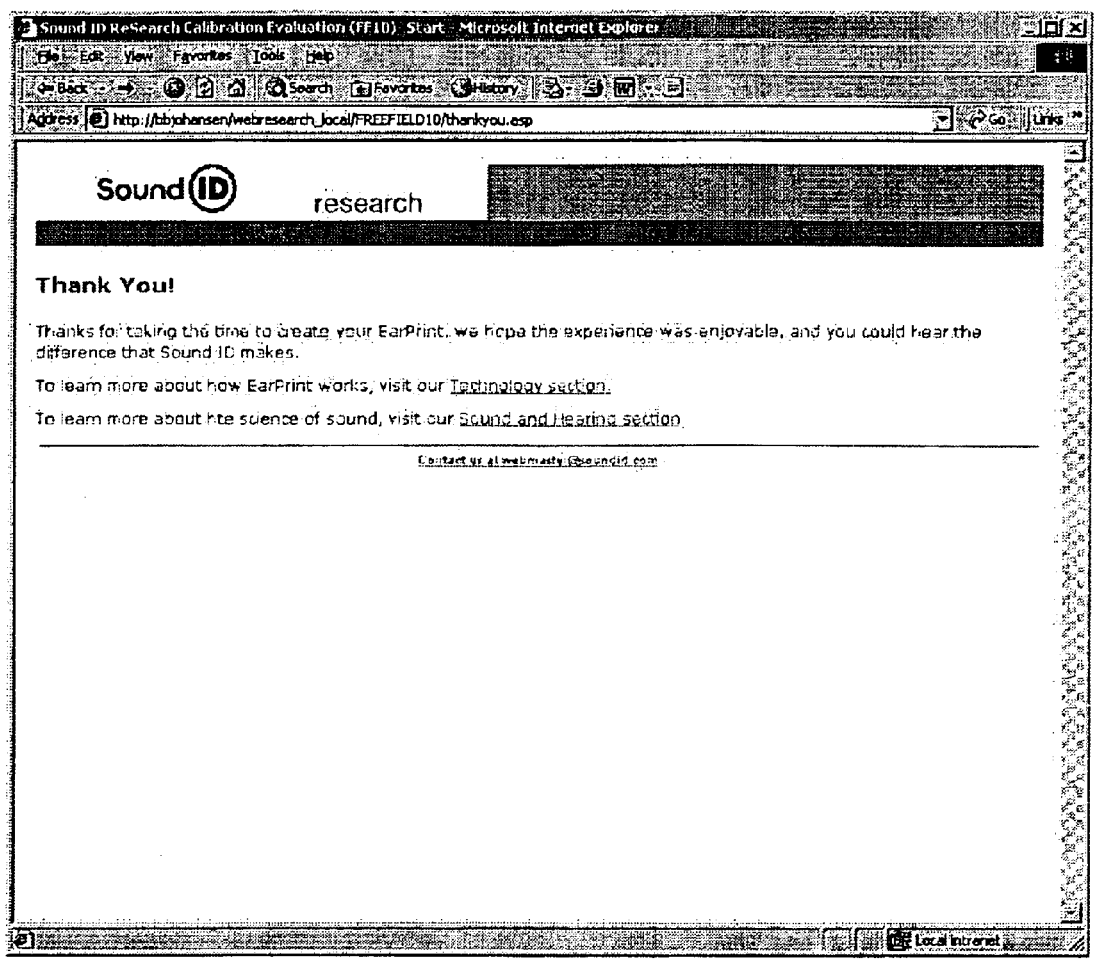

When the process is done, the web page of FIG. 24 is presented which acts as a closing presentation for the process.

The interactive presentation shown in FIGS. 11 through 24 is adapted for presentation using a full function browser in a personal computer with a large format display, and coupled to the Internet. In other types of consumer devices, such as mobile phones or personal digital assistants, the presentation is adapted to the format of the display available. Also, the types of software components that are downloaded from the server to the remote device to support the hearing test are adapted to be architecture of the platforms used during the testing process.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the appended claims.

What is claimed is:

1. A method for conducting a hearing test using a computer program, comprising:

establishing a communication channel between a remote device and a server in a communication network;

executing a first component of the computer program at the server; and executing a second component of the computer program at the remote device, wherein the computer program comprises a routine that manages interaction via an interface on the remote device, and adaptively selects stimuli based upon said interaction to be produced at the remote device far said interaction according to a convergent process to determine a hearing characteristic, wherein said convergent process comprises a maximum likelihood procedure, and wherein said routine includes causing a visual effect at the device corresponding to each of N alternative stimulus intervals, causing generation of a selected stimulus during one of the N alternative stimulus intervals, and prompting a subject to make a choice by selecting a visual effect indicating the subject's perception of the stimulus during said N alternative stimulus intervals, and said convergent process comprises selecting a first stimulus and producing a subsequent stimulus that is reduced in magnitude by a step amount if the choice in the interaction identifies a correct interval a number X times, or producing a subsequent stimulus that is increased in magnitude by a step amount if the choice in the interaction identifies an incorrect interval a number Y times, and wherein at least one of X and Y is greater than 1 during at least a part of the convergent process.

2. The method of claim 1, wherein said interaction comprises an N-alternative forced choice interaction.

3. The method of claim 1, wherein the communication network comprises a packet switched network.

4. The method of claim 1, wherein the communication network comprises a network executing according a standard internet protocol.

5. The method of claim 1, wherein the channel comprises a connection according to a standard transmission control protocol over a standard internet protocol (TCP/IP).

6. The method of claim 1, wherein the channel comprises a link through a cellular telephone network.

7. The method of claim 1, wherein the channel comprises a link through a pager network.

8. The method of claim 1, wherein the remote device comprises a mobile phone.

9. The method of claim 1, wherein the remote device comprises a home computer.

10. The method of claim 1, wherein the remote device comprises a hand held computing platform.

11. The method of claim 1, wherein said routine to manage interaction includes:

logic providing graphic constructs for display at the device corresponding to each of N alternative stimulus intervals.

12. The method of claim 1, wherein said convergent process comprises a staircase function.

13. The method of claim 1, wherein the number X equals 1, and the number Y equals 1 during an initial part of the convergent process, and wherein at least one of the number X and the number Y is changed to a value greater than 1 during a subsequent part of the convergent process.

14. The method of claim 1, wherein the N is in the range of 2 to 4.

15. The method of claim 1, wherein said convergent process comprises:

selecting a first stimulus in response to a base line threshold, producing a subsequent stimulus that is reduced in magnitude by a first downward step amount if the choice in the interaction identifies a correct interval a number X times, or producing a subsequent stimulus that is increased in magnitude by a first upward step amount if the choice in the interaction identifies an incorrect interval a number Y times; and after a number A of reversals of direction of the step direction, producing a subsequent stimulus that is reduced in magnitude by a second downward step amount if the choice in the interaction identifies a correct interval a number X times, or producing a subsequent stimulus that is increased in magnitude by a second upward step amount if the choice in the interaction identifies an incorrect interval a number Y times, wherein either the second downward step amount is less than the first downward step amount, or the second upward step amount is less than the first upward step amount, or both the second downward step amount is less than the first downward step amount, and the second upward step amount is less than the first upward step amount.

16. A method for conducting a hearing test using a computer program, comprising:

establishing a communication channel between a remote device and a server in a communication network;

executing a first component of the computer program at the server, and executing a second component of the computer program at the remote device, wherein the computer program comprises a routine that manages interaction via an interface on the remote device, and adaptively selects stimuli based upon said interaction to be produced at the remote device for said interaction according to a convergent process to determine a hearing characteristic, wherein said routine includes causing a visual effect at the device corresponding to each of N alternative stimulus intervals, causing generation of a selected stimulus during one of the N alternative stimulus intervals, and promoting a subject to make a choice by selecting a visual effect indicating the subject's perception of the stimulus during said N alternative stimulus intervals, and said convergent process comprises selecting a first stimulus and producing a subsequent stimulus that is reduced in magnitude by a step amount if the choice in the interaction identifies a correct interval a number X times, or producing a subsequent stimulus that is increased in magnitude by a step amount if the choice in the interaction identifies an incorrect interval a number Y times, and wherein at least one of X and Y is greater than 1 during at least a part of the convergent process, wherein the number X equals 3, and the number Y equals 1.

17. A method for conducting a hearing test using a computer program, comprising:

establishing a communication channel between a remote device and a server in a communication network;

executing a first component of the computer program at the server; and executing a second component of the computer program at the remote device, wherein the computer program comprises a routine that manages interaction via an interface on the remote device, and adaptively selects stimuli based upon said interaction to be produced at the remote device for said interaction according to a convergent process to determine a hearing characteristic, wherein said routine includes causing a visual effect at the device corresponding to each of N alternative stimulus intervals, causing generation of a selected stimulus during one of the N alternative stimulus intervals, and promoting a subject to make a choice by selecting a visual effect indicating the subject's perception of the stimulus during said N alternative stimulus intervals, and said convergent process comprises selecting a first stimulus and producing a subsequent stimulus that is reduced in magnitude by a step amount if the choice in the interaction identifies a correct interval a number X times, or producing a subsequent stimulus that is increased in magnitude by a step amount if the choice in the interaction identifies an incorrect interval a number Y times, and wherein at least one of X and Y is greater than 1 during at least a part of the convergent process, wherein N equals 2, and the number X equals 3, and the number Y equals 1.

18. An apparatus comprising:

a data processor which executes instructions;

a communication interface coupled to the data processor; and memory coupled to the data processor which stores instructions in a form readable by the data processor, the instructions specifying processes which establish a communication channel with a remote device via the communication interface and manage presentation of an interaction with a test subject via an interface on the remote device, and adaptively select stimuli based upon said interaction to be produced at the remote device for said interaction according to a convergent process to determine a hearing characteristic, wherein said convergent process comprises a maximum likelihood procedure, and wherein said processes which manage presentation of said interaction include:

causing a visual effect at the device corresponding to each of N alternative stimulus intervals, causing generation of a selected stimulus during one of the N alternative stimulus intervals, and prompting the test subject to make a choice by selecting a visual effect indicating perception of the stimulus during said N alternative stimulus intervals; and said convergent process comprises selecting a first stimulus in response to a base line threshold, producing a subsequent stimulus that is reduced in magnitude by a step amount if the choice in the interaction identifies a correct interval a number X times, or producing a subsequent stimulus that is increased in magnitude by a step amount if the choice in the interaction identifies an incorrect interval a number Y times, where at least one of X and Y is greater than 1 during at least a part of the convergent process.

19. The apparatus of claim 18, wherein said interaction comprises an N-alternative forced choice interaction.

20. The apparatus of claim 18, wherein the communication channel comprises a link via a packet switched network.

21. The apparatus of claim 18, wherein the communication channel comprises a link via a network executing according a standard internet protocol.

22. The apparatus of claim 18, wherein the communication channel comprises a connection according to a standard transmission control protocol over a standard internet protocol (TCP/IP).

23. The apparatus of claim 18, wherein the communication channel comprises a link through a cellular telephone network.

24. The apparatus of claim 18, wherein the communication channel comprises a link through a pager network.

25. The apparatus of claim 18, wherein the remote device comprises a mobile phone.

26. A The apparatus of claim 18, wherein the remote device comprises a home computer.

27. The apparatus of claim 18, wherein the remote device comprises a hand held computing platform.

28. The apparatus of claim 18, wherein said processes which manage presentation of said interaction include:
logic providing graphic constructs for display at the device corresponding to each of N alternative stimulus intervals.

29. The apparatus of claim 18, wherein said convergent process comprises a staircase function.

30. The apparatus of claim 18, wherein the number X equals 1, and the number Y equals 1 during an initial part of the convergent process, and wherein at least one of the number X and the number Y is changed to a value greater than 1 during a subsequent part of the convergent process.

31. The apparatus of claim 18, wherein the N is in the range of 2 to 4.

32. The apparatus of claim 18, wherein said convergent process comprises:
selecting a first stimulus in response to said base line threshold, producing a subsequent stimulus that is reduced in magnitude by a first downward step amount if the choice in the interaction identifies a correct interval a number X times, or producing a subsequent stimulus that is increased in magnitude by a first upward step amount if the choice in the interaction identifies an incorrect interval a number Y times; and
after a number A of reversals of direction of the step direction, producing a subsequent stimulus that is reduced in magnitude by a second downward step amount if the choice in the interaction identifies a correct interval a number X times, or producing a subsequent stimulus that is increased in magnitude by a second upward step amount if the choice in the interaction identifies an incorrect interval a number Y times, wherein either the second downward step amount is less than the first downward step amount, or the second upward step amount is less than the first upward step amount, or both the second downward step amount is less than the first downward step amount, and the second upward step amount is less than the first upward step amount.

33. The apparatus of claim 18, wherein said processes include routines for downloading a software component to the remote device used during said interaction.

34. An apparatus comprising:
a data processor which executes instructions;
a communication interface coupled to the data processor; and
memory coupled to the data processor which stores instructions in a form readable by the data processor, the instructions specifying processes which establish a communication channel with a remote device via the communication interface and manage presentation of an interaction with a test subject via an interface on the remote device, and adaptively select stimuli based upon said interaction to be produced at the remote device for said interaction according to a convergent process to determine a hearing characteristic, wherein said convergent process comprises a maximum likelihood procedure, and
wherein said processes which manage presentation of said interaction include:
causing a visual effect at the device corresponding to each of N alternative stimulus intervals, causing generation of a selected stimulus during one of the N alternative stimulus intervals, and prompting the subject to make a choice by selecting a visual effect indicating perception of the stimulus during said N alternative stimulus intervals; and
said convergent process comprises selecting a first stimulus in response to a base line threshold, producing a subsequent stimulus that is reduced in magnitude by a step amount if the choice in the interaction identifies a correct interval a number X times, or producing a subsequent stimulus that is increased in magnitude by a step amount if the choice in the interaction identifies an incorrect interval a number Y times, where at least one of X and Y is greater than 1 during at least a part of the convergent process, wherein the number X equals 3, and the number Y equals 1.

35. An apparatus comprising:
a data processor which executes instructions;
a communication interface coupled to the data processor; and
memory coupled to the data processor which stores instructions in a form readable by the data processor, the instructions specifying processes which establish a communication channel with a remote device via the communication interface and manage presentation of an interaction with a test subject via an interface on the remote device, and adaptively select stimuli based upon said interaction to be produced at the remote device for said interaction according to a convergent process to determine a hearing characteristic, wherein said convergent process comprises a maximum likelihood procedure, and wherein said processes which manage presentation of said interaction include:

causing a visual effect at the device corresponding to each of N alternative stimulus intervals, causing generation of a selected stimulus during one of the N alternative stimulus intervals, and prompting the subject to make a choice by selecting a visual effect indicating perception of the stimulus during said N alternative stimulus intervals; and said convergent process comprises selecting a first stimulus in response to a base line threshold, producing a subsequent stimulus that is reduced in magnitude by a step amount if the choice in the interaction identifies a correct interval a number X times, or producing a subsequent stimulus that is increased in magnitude by a step amount if the choice in the interaction identifies an incorrect interval a number Y times, where at least one of X and Y is greater than 1 during at least a part of the convergent process, wherein N equals 2, and the number X equals 3, and the number Y equals 1.

36. A method for remotely testing hearing using a consumer electronics device having a communication interface, an audio stimulus generator and an input, comprising:

remotely establishing a base line threshold for a control signal supplied via the communication interface causing the device to generate a sound;

remotely managing an N-alternative forced choice stimulus and response interaction to a subject; and adaptively producing signals to induce selected stimuli at the device for said interaction according to a convergent, maximum likelihood process based upon said base line threshold and said interaction to determine a hearing characteristic.

37. The method of claim 36, wherein said remotely managing includes:

providing graphic constructs for display at the device corresponding to each of N alternative stimulus intervals, the graphic constructs being aligned in an up and down relationship, causing generation of a selected stimulus during one of the N alternative stimulus intervals, and prompting the subject to make a choice by selecting a graphic construct using an input device indicating the subject's perception of the stimulus during said N alternative stimulus intervals.

38. The method of claim 36, wherein said remotely managing includes:

causing a visual effect at the device corresponding to each of N alternative stimulus intervals, causing generation of a selected stimulus during one of the N alternative stimulus intervals, and prompting the subject to make a choice by selecting a visual effect indicating the subject's perception of the stimulus during said N alternative stimulus intervals.

39. The method of claim 36, wherein said convergent process comprises a staircase function.

40. The method of claim 38, wherein said convergent process comprises selecting a first stimulus in response to said base line threshold, producing a subsequent stimulus that is reduced in magnitude by a step amount if the choice in the interaction identifies a correct interval, a number X times, or a producing a subsequent stimulus that is increased in magnitude by a step amount if the choice in the interaction identifies an incorrect interval a number Y times, where at least one of X and Y is greater than 1 during at least part of the convergent, maximum likelihood process.

41. The method of claim 40, wherein the number X equals 3, and the number Y equals 1.

42. The method of claim 40, wherein the number X equals 1, and the number Y equals 1 during an initial part of the convergent process, and wherein at least one of the number X and the number Y is changed to a value greater than 1 during a subsequent part of the convergent process.

43. The method of claim 40, wherein N equals 2, and the number X equals 3, and the number Y equals 1.

44. The method of claim 36, wherein the N is in the range of 2 to 4.

45. The method of claim 36, wherein said convergent process comprises:

selecting a first stimulus in response to said base line threshold, producing a subsequent stimulus that is reduced in magnitude by a first downward step amount if a response in the interaction identities a correct interval a number X times, or producing a subsequent stimulus that is increased in magnitude by a first upward step amount if the response in the interaction identifies an incorrect interval a number Y times, and after a number A of reversals of direction of the step direction, producing a subsequent stimulus that is reduced in magnitude by a second downward step amount if the response in the interaction identifies a correct interval a number X times, or producing a subsequent stimulus that is increased in magnitude by a second upward step amount if the response in the interaction identifies an incorrect interval a number Y times, wherein either the second downward step amount is less than the first downward step amount, or the second upward step amount is less than the first upward step amount, or both the second downward step amount is less than the first downward step amount, and the second upward step amount is less than the first upward step amount.

46. The method of claim 36, wherein said remotely establishing comprises communication via a communication network.

47. The method of clam 36, wherein said remotely managing comprises communication via a communication network.

48. The method of claim 36, including downloading a software component from a server to the remote device which upon execution supports said method.

* * * * *